US011982678B2

(12) United States Patent
Chiu et al.

(10) Patent No.: US 11,982,678 B2
(45) Date of Patent: May 14, 2024

(54) ENSEMBLE-DECISION ALIQUOT RANKING

(71) Applicant: UNIVERSITY OF WASHINGTON THROUGH ITS CENTER FOR COMMERCIALIZATION, Seattle, WA (US)

(72) Inventors: Daniel T. Chiu, Seattle, WA (US); Perry G. Schiro, Seattle, WA (US); Jason S. Kuo, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 1275 days.

(21) Appl. No.: 16/171,918

(22) Filed: Oct. 26, 2018

(65) Prior Publication Data

US 2019/0120857 A1 Apr. 25, 2019

Related U.S. Application Data

(62) Division of application No. 13/257,571, filed as application No. PCT/US2010/030938 on Apr. 13, 2010, now abandoned.

(60) Provisional application No. 61/168,892, filed on Apr. 13, 2009.

(51) Int. Cl.
*G01N 33/58* (2006.01)
*G01N 21/25* (2006.01)
*G01N 22/00* (2006.01)
*G01N 33/53* (2006.01)
*G01N 33/574* (2006.01)
*G01N 33/68* (2006.01)
G01N 15/1433 (2024.01)
G01N 21/64 (2006.01)

(52) U.S. Cl.
CPC ......... *G01N 33/6893* (2013.01); *G01N 21/25* (2013.01); *G01N 22/00* (2013.01); *G01N 33/5302* (2013.01); *G01N 33/5308* (2013.01); *G01N 33/57407* (2013.01); *G01N 33/582* (2013.01); *G01N 15/1433* (2024.01); *G01N 21/64* (2013.01); *Y02A 50/30* (2018.01)

(58) Field of Classification Search
CPC ......... G01N 33/57407; G01N 33/5302; G01N 33/5308; G01N 22/00; G01N 33/6893; G01N 21/25; G01N 33/582; G01N 15/1475; G01N 21/64; Y02A 50/30
See application file for complete search history.

(56) References Cited

U.S. PATENT DOCUMENTS

| 5,602,042 A | 2/1997 | Farber |
|---|---|---|
| 6,150,173 A | 11/2000 | Schubert |
| 6,365,362 B1 | 4/2002 | Terstappen et al. |
| 7,745,221 B2 | 6/2010 | Butler et al. |
| 2002/0037499 A1 | 3/2002 | Quake et al. |
| 2002/0081569 A1 | 6/2002 | Anderson |
| 2003/0175980 A1 | 9/2003 | Hayenga et al. |
| 2003/0232425 A1 | 12/2003 | Bachalo et al. |
| 2004/0072278 A1 | 4/2004 | Chou et al. |
| 2005/0103690 A1 | 5/2005 | Kawano et al. |
| 2006/0078888 A1 | 4/2006 | Griffiths et al. |
| 2006/0266679 A1 | 11/2006 | Bohm et al. |
| 2007/0025883 A1 | 2/2007 | Tai et al. |
| 2007/0037172 A1 | 2/2007 | Chiu et al. |
| 2007/0172954 A1 | 7/2007 | Ismagilov et al. |
| 2008/0003142 A1 | 1/2008 | Link et al. |
| 2008/0145286 A1 | 6/2008 | Maltezos et al. |
| 2008/0163946 A1 | 7/2008 | Gomez et al. |
| 2008/0248499 A1 | 10/2008 | Chiu et al. |
| 2008/0261295 A1 | 10/2008 | Butler et al. |
| 2008/0318324 A1 | 12/2008 | Chiu et al. |
| 2009/0014360 A1 | 1/2009 | Toner et al. |
| 2009/0035838 A1 | 2/2009 | Quake et al. |
| 2010/0055766 A1 | 3/2010 | Hwang et al. |
| 2010/0279321 A1 | 11/2010 | Chiu et al. |
| 2012/0015347 A1 | 1/2012 | Singhal et al. |
| 2012/0129190 A1 | 5/2012 | Chiu et al. |
| 2014/0073042 A1 | 3/2014 | Igata |
| 2016/0146823 A1 | 5/2016 | Chiu et al. |

FOREIGN PATENT DOCUMENTS

| CN | 102015998 A | 4/2011 |
|---|---|---|
| JP | S6182168 A | 4/1986 |
| JP | 2003294604 A | 10/2003 |

(Continued)

OTHER PUBLICATIONS

Gross et al. Detection of rare cells at a frequency of one per million by flow cytometry. Cytometry 1993, vol. 14, pp. 519-526. (Year: 1993).*
Huh et al. Microfluidics for flow cytometric analysis of cells and particles. Physiol. Meas 2005, vol. 26, pp. 73-98 (Year: 2005).*
Adams, et al. Highly efficient circulating tumor cell isolation from whole blood and label-free enumeration using polymer-based microfluidics with an integrated conductivity sensor. J Am Chem Soc. Jul. 9, 2008;130(27):8633-41. doi: 10.1021/ja8015022. Epub Jun. 17, 2008.

(Continued)

*Primary Examiner* — Shafiqul Haq
(74) *Attorney, Agent, or Firm* — Christensen O'Connor Johnson Kindness PLLC

(57) ABSTRACT

Provided herein, among other aspects, are methods and apparatuses for ranking aliquots from a suspension containing bioparticles. In certain embodiments, the bioparticles may be cells, organelles, proteins, DNAs, debris of biological origin, microbeads coated with biological compounds, or viral particles. As such, the methods and apparatuses provided herein may be used to quantify rare cells such as circulating cancer cells, fetal cells and other rare cells present in bodily fluids for disease diagnosis, prognosis, or treatment.

9 Claims, 16 Drawing Sheets

(56) References Cited

FOREIGN PATENT DOCUMENTS

| JP | 2005245317 A | 9/2005 |
|---|---|---|
| JP | 2008516251 A | 5/2008 |
| JP | 2009063375 A | 3/2009 |
| KR | 20050047540 A | 5/2005 |
| TW | 574130 B | 2/2004 |
| WO | WO-02/097122 A1 | 12/2002 |
| WO | WO-2006067715 A2 | 6/2006 |
| WO | WO-2006110855 A2 | 10/2006 |
| WO | WO-2007081387 A1 | 7/2007 |
| WO | WO-2008130871 A2 | 10/2008 |
| WO | WO-2009128948 A1 | 10/2009 |
| WO | WO-2010120818 A2 | 10/2010 |
| WO | WO-2011063416 A2 | 5/2011 |
| WO | WO-2012162779 A1 | 12/2012 |
| WO | WO-2015002975 A1 | 1/2015 |

OTHER PUBLICATIONS

Adams, et al. Integrated acoustic and magnetic separation in microfluidic channels. Appl Phys Lett. Dec. 21, 2009;95(25):254103.

Aktas, et al. Stem cell and epithelial-mesenchymal transition markers are frequently overexpressed in circulating tumor cells of metastatic breast cancer patients. Breast Cancer Res. 2009;11(4):R46. doi: 10.1186/bcr2333. Epub Jul. 9, 2009.

Al-Hajj, et al. Prospective identification of tumorigenic breast cancer cells. Proc Natl Acad Sci USA. Apr. 1, 2003;100(7):3983-8. Epub Mar. 10, 2003.

Allard, et al. Tumor cells circulate in the peripheral blood of all major carcinomas but not in healthy subjects or patients with nonmalignant diseases. Clin Cancer Res. Oct. 15, 2004;10(20):6897-904.

Alsalameh, et al. Identification of mesenchymal progenitor cells in normal and osteoarthritic human articular cartilage. Arthritis Rheum. May 2004;50(5):1522-32.

Alunni-Fabbroni, et al. Circulating tumour cells in clinical practice: Methods of detection and possible characterization. Methods. Apr. 2010;50(4):289-97. doi: 10.1016/j.ymeth.2010.01.027. Epub Jan. 29, 2010. Review.

Andreopoulou, et al. Circulating tumor cells as prognostic marker in metastatic breast cancer. Expert Rev Anticancer Ther. Feb. 2010; 10(2):171-7. doi: 10.1586/era.09.105.

Aurilio, et al. Prognostic value of circulating tumor cells in primary and metastatic breast cancer. Expert Rev Anticancer Ther. Feb. 2012;12(2):203-14. doi: 10.1586/era.11.208.

Balasubramanian, et al. β3 integrin in cardiac fibroblast is critical for extracellular matrix accumulation during pressure overload hypertrophy in mouse. PLoS One. 2012;7(9):e45076. doi: 10.1371/journal.pone.0045076. Epub Sep. 1, 20122.

Balasubramanian, et al. Confocal images of circulating tumor cells obtained using a methodology and technology that removes normal cells. Mol Pharm. Sep.-Oct. 2009;6(5):1402-8. doi: 10.1021/mp9000519.

Bode, et al. Toponome imaging system (TIS): imaging the proteome with functional resolution. Nature Methods. Jan. 2007; iii-iv.

Chaffer, et al. A perspective on cancer cell metastasis. Science. Mar. 25, 2011;331(6024):1559-64. doi: 10.1126/science.1203543.

Chinese Office Action dated May 3, 2018 for CN Application No. 201480048902.

"Schiro, et al. Sensitive and high-throughput isolation of rare cells from peripheral blood with ensemble-decision aliquot ranking. Angew Chem Int Ed Engl. May 7, 2012;51(19):4618-22. doi: 10.1002/anie.201108695. Epub Feb. 22, 2012. (With Supporting Information, total 17 pages)".

CN 201480048902.0 Third Office Action dated May 3, 2018 (w/ English translation).

Cohen, et al. Relationship of circulating tumor cells to tumor response, progression-free survival, and overall survival in patients with metastatic colorectal cancer. J Clin Oncol. Jul. 1, 2008;26(19):3213-21. doi: 10.1200/JCO.2007.15.8923.

Cristofanilli, et al. Circulating tumor cells, disease progression, and survival in metastatic breast cancer. N Engl J Med. Aug. 19, 2004;351(8):781-91.

Cristofanilli, et al. Circulating tumor cells in breast cancer: Advanced tools for "tailored" therapy? Proc Natl Acad Sci U S A. Nov. 14, 2006;103(46):17073-4. Epub Nov. 7, 2006.

Danila, et al. Circulating tumor cells as biomarkers in prostate cancer. Clin Cancer Res. Jun. 15, 2011;17(12):3903-12. doi: 10.1158/1078-0432.CCR-10-2650.

De Bono, et al. Translating cancer research into targeted therapeutics. Nature. Sep. 30, 2010;467(7315):543-9. doi: 10.1038/nature09339.

Dharmasiri, et al. High-throughput selection, enumeration, electrokinetic manipulation, and molecular profiling of low-abundance circulating tumor cells using a microfluidic system. Anal Chem. Mar. 15, 2011;83(6):2301-9. doi: 10.1021/ac103172y. Epub Feb. 14, 2011.

Dharmasiri, et al. Microsystems for the capture of low-abundance cells. Annu Rev Anal Chem (Palo Alto Calif). 2010;3:409-31. doi: 10.1146/annurev.anchem.111808.073610.

Edgar, et al. Compartmentalization of chemically separated components into droplets. Angew Chem Int Ed Engl. 2009;48(15):2719-22. doi: 10.1002/anie.200805396.

European office action dated Sep. 27, 2016 for EP Application No. 15188512.6.

European search report dated Sep. 6, 2012 for EP Application No. 10765047.5.

European search report dated Dec. 10, 2015 for EP Application No. 15188512.6.

Evans, et al. Toponome imaging system: multiplex biomarkers in oncology. Trends Mol Med. Dec. 2012;18(12):723-31. doi: 10.1016/j.molmed.2012.10.003. Epub Nov. 2, 2012.

"Extended European Search Report and Search Opinion dated Dec. 13, 2017 for European Patent Application No. EP17187038.9".

Fidler. The pathogenesis of cancer metastasis: the 'seed and soil' hypothesis revisited. Nat Rev Cancer. Jun. 2003;3(6):453-8.

Fiorini, et al. Disposable microfluidic devices: fabrication, function, and application. Biotechniques. Mar. 2005;38(3):429-46.

Fokas, et al. Metastasis: the seed and soil theory gains identity. Cancer Metastasis Rev. Dec. 2007;26(3-4):705-15.

Friel, et al. Relevance of circulating tumor cells, extracellular nucleic acids, and exosomes in breast cancer. Breast Cancer Res Treat. Oct. 2010;123(3):613-25. doi: 10.1007/s10549-010-0980-2. Epub Jun. 15, 2010.

Goda, et al. High-throughput single-microparticle imaging flow analyzer. Proc Natl Acad Sci U S A. Jul. 17, 2012;109(29):11630-5. doi: 10.1073/pnas.1204718109. Epub Jul. 2, 2012.

Gorges, et al. Circulating tumour cells escape from EpCAM-based detection due to epithelial-to-mesenchymal transition. BMC Cancer. May 16, 2012;12:178. doi: 10.1186/1471-2407-12-178.

Gossett, et al. Label-free cell separation and sorting in microfluidic systems. Anal Bioanal Chem. Aug. 2010;397(8):3249-67. doi: 10.1007/s00216-010-3721-9. Epub Apr. 25, 2010.

Gross, et al. Detection of rare cells at a frequency of one per million by flow cytometry. Cytometry. 1993;14(5):519-26.

Gross, et al. Model study detecting breast cancer cells in peripheral blood mononuclear cells at frequencies as low as 10(-7). Proc Natl Acad Sci U S A. Jan. 17, 1995;92(2):537-41.

Guetta, et al. Analysis of fetal blood cells in the maternal circulation: challenges, ongoing efforts, and potential solutions. Stem Cells Dev. Feb. 2004;13(1):93-9.

Hoshino, et al. Microchip-based immunomagnetic detection of circulating tumor cells. Lab Chip. Oct. 21, 2011;11(20):3449-57. doi: 10.1039/c1lc20270g. Epub Aug. 24, 2011.

Hou, et al. Circulating tumor cells as a window on metastasis biology in lung cancer. Am J Pathol. Mar. 2011;178(3):989-96. doi: 10.1016/j.ajpath.2010.12.003.

Hsieh, et al. High speed detection of circulating tumor cells. Biosens Bioelectron. Apr. 15, 2006;21(10):1893-9. Epub Feb. 7, 2006.

Hulme, et al. Incorporation of prefabricated screw, pneumatic, and solenoid valves into microfluidic devices. Lab Chip. Jan. 7, 2009;9(1):79-86. doi: 10.1039/b809673b. Epub Oct. 21, 2008.

(56) References Cited

OTHER PUBLICATIONS

International search report and written opinion dated Nov. 7, 2014 for PCT/US2014/045094.
International search report and written opinion dated Nov. 26, 2010 for PCT/US2010/030938.
Issadore, et al. Ultrasensitive clinical enumeration of rare cells ex vivo using a micro-hall detector. Sci Transl Med. Jul. 4, 2012;4(141):141ra92. doi: 10.1126/scitranslmed.3003747.
Jaggupilli, et al. Significance of CD44 and CD24 as cancer stem cell markers: an enduring ambiguity. Clin Dev Immunol. 2012;2012:708036. doi: 10.1155/2012/708036. Epub May 30, 2012.
Japanese Office Action dated May 11, 2018 for JP201718205 (with English Translation).
Jeffries, et al. Ultrasensitive and high-throughput fluorescence analysis of droplet contents with orthogonal line confocal excitation. Anal Chem. Dec. 1, 2010;82(23):9948-54. doi: 10.1021/ac102173m. Epub Nov. 9, 2010.
Kahn, et al. Enumeration of circulating tumor cells in the blood of breast cancer patients after filtration enrichment: correlation with disease stage. Breast Cancer Res Treat. Aug. 2004;86(3):237-47.
Khoja, et al. A pilot study to explore circulating tumour cells in pancreatic cancer as a novel biomarker. Br J Cancer. Jan. 31, 2012;106(3):508-16. doi: 10.1038/bjc.2011.545. Epub Dec. 20, 2011.
Kirby, et al. Functional characterization of circulating tumor cells with a prostate-cancer-specific microfluidic device. PLoS One. 2012;7(4):e35976. doi: 10.1371/journal.pone.0035976. Epub Apr. 27, 2012.
Krivacic, et al. A rare-cell detector for cancer. Proc Natl Acad Sci U S A. Jul. 20, 2004;101(29):10501-4. Epub Jul. 12, 2004.
"Kruger et al. Development of a microfluidic device for fluorescence activated cell sorting, 2002, Journal of Micrornechanics and Microengineering, 12:486-494.".
Kuo, et al. Deformability considerations in filtration of biological cells. Lab Chip. Apr. 7, 2010;10(7):837-42. doi: 10.1039/b922301k. Epub Jan. 19, 2010.
Lara, et al. Enrichment of rare cancer cells through depletion of normal cells using density and flow-through, immunomagnetic cell separation. Exp Hematol. Oct. 2004; 32(10): 891-904.
Lee, et al. Polymethylhydrosiloxane (PMHS) as a functional material for microfluidic chips. J Micromech Microeng. 2008; 18:025026.
Li, et al. Probing circulating tumor cells in microfluidics. Lab Chip. Feb. 21, 2013;13(4):602-9. doi: 10.1039/c2lc90148j.
Lianidou, et al. Molecular characterization of circulating tumor cells in breast cancer: challenges and promises for individualized cancer treatment. Cancer Metastasis Rev. Dec. 2012;31(3-4):663-71. doi: 10.1007/s10555-012-9366-8.
Lin, et al. Portable filter-based microdevice for detection and characterization of circulating tumor cells. Clin Cancer Res. Oct. 15, 2010;16(20):5011-8. doi: 10.1158/1078-0432.CCR-10- 1105. Epub Sep. 28, 2010.
Lorenz, et al. Simultaneous generation of multiple aqueous droplets in a microfluidic device. Anal Chim Acta. Dec. 23, 2008;630(2):124-30. doi: 10.1016/j.aca.2008.10.009. Epub Oct. 14, 2008.
Lucci, et al. Circulating tumour cells in non-metastatic breast cancer: a prospective study. Lancet Oncol. Jul. 2012;13(7):688-95. doi: 10.1016/S1470-2045(12)70209-7. Epub Jun. 6, 2012.
Maheswaran, et al. Detection of mutations in EGFR in circulating lung-cancer cells. N Engl J Med. Jul. 24, 2008;359(4):366-77. doi: 10.1056/NEJMoa0800668. Epub Jul. 2, 2008.
Martin, et al. DNA labeling in living cells. Cytometry Part A. 2005; 67A(1):45-52.
McCafferty, et al. Phage antibodies: filamentous phage displaying antibody variable domains. Nature. Dec. 6, 1990;348(6301):552-4.
Mocellin, et al. Circulating tumor cells: the 'leukemic phase' of solid cancers. Trends Mol Med. Mar. 2006;12(3):130-9. Epub Feb. 20, 2006.
Mostert, et al. Circulating tumor cells (CTCs): detection methods and their clinical relevance in breast cancer. Cancer Treat Rev. Aug. 2009;35(5):463-74. doi: 10.1016/j.ctrv.2009.03.004. Epub May 1, 2009.
Nagrath, et al. Isolation of rare circulating tumour cells in cancer patients by microchip technology. Nature. Dec. 20, 2007;450(7173):1235-9.
"Office action dated Jan. 4, 2017 for CA Application No. 2,758,382".
Zhao, et al. Method for the accurate preparation of cell-spiking standards. Anal Chem. Feb. 1, 2009;81(3):1285-90. doi: 10.1021/ ac802250d.
Zheng et al. Membrane microfilter device for selective capture, electrolysis and genomic analysis of human circulating tumor cells. J Chromatogr A 1162(2):154-161 (2007).
Zieglschmid, et al. Detection of disseminated tumor cells in peripheral blood. Crit Rev Clin Lab Sci. 2005;42(2):155-96.
Office action dated Apr. 26, 2016 for CA Application No. 2,758,382.
Zhao, et al. Imaging multiple biomarkers in captured rare cells by sequential immunostaining and photobleaching. Methods. Dec. 1, 2013;64(2):108-13. doi: 10.1016/j.ymeth.2013.08.006. Epub Aug. 13, 2013.
"Office action dated Jun. 16, 2017 for CN Application No. 201510585927".
Zhao, et al. An automated high-throughput counting method for screening circulating tumor cells in peripheral blood. Anal Chem. Feb. 19, 2013;85(4):2465-71. doi: 10.1021/ac400193b. Epub Feb. 6, 2013.
Zhao et al. Flow cytometry. Principles and Methods for Histiocyte Molecular Experiment. China Press of Traditional Chinese Medicine. p. 324-327. Sep. 30, 2003. (in Chinese with English translation).
Office action dated Jul. 23, 2018 for U.S. Appl. No. 14/903,012.
Zhang. The introduction of the flow cytometer. Construction and Working Principles of Flow Cytometer. Information of Medical Equipment. 20(8):25-26. Aug. 31, 2005. (in Chinese with English abstract).
Office Action dated Aug. 3, 2016 for JP Application No. 2015- 83992.
"Office action dated Aug. 16, 2017 for CN Application No. 201480048902.0".
"Office action dated Aug. 30, 2016 for CN Application No. 201510585927.0".
Zabaglo, et al. Cell filtration-laser scanning cytometry for the characterisation of circulating breast cancer cells. Cytometry Part A 55A, 102-108 (2003).
"Office action dated Sep. 14, 2017 for JP Application No. 2017- 18205".
"Office Action dated Oct. 19, 2017 for CN Patent Application No. 201510585927.0".
Office action dated Nov. 10, 2016 for AU Application No. 2015234379.
Office action dated Nov. 17, 2016 for CN Application No. 201480048902.
"Office Action dated Nov. 21, 2017 for KR Patent Application No. KR-2011-7027042".
Office Action dated Nov. 24, 2015 for JP Application No. 2015- 83992.
Yu, et al. Circulating breast tumor cells exhibit dynamic changes in epithelial and mesenchymal composition. Science. Feb. 1, 2013;339(6119):580-4. doi: 10.1126/science.1228522.
Oudejans, et al. Circulating trophoblast in maternal blood. Prenat Diagn. Feb. 2003;23(2):111-6. Review.
Pantel, et al. Cancer micrometastases. Nature Reviews Clinical Oncology. 2009; 6(6):339-351.
Paterlini-Brechot, et al. Circulating tumor cells (CTC) detection: clinical impact and future directions. Cancer Lett. Aug. 18, 2007;253(2):180-204. Epub Feb. 20, 2007.
Patriarca, et al. Epithelial cell adhesion molecule expression (CD326) in cancer: a short review. Cancer Treat Rev. Feb. 2012;38(1):68-75. doi: 10.1016/j.ctrv.2011.04.002. Epub May 14, 2011.
Payne, et al. Measurements of EGFR expression on circulating tumor cells are reproducible over time in metastatic breast cancer patients. Pharmacogenomics. Jan. 2009;10(1):51-7. doi: 10.2217/ 14622416.10.1.51.

(56) References Cited

OTHER PUBLICATIONS

Pinzani, et al. Isolation by size of epithelial tumor cells in peripheral blood of patients with breast cancer: correlation with real-time reverse transcriptase-polymerase chain reaction results and feasibility of molecular analysis by laser microdissection. Hum Pathol. Jun. 2006;37(6):711-8.
Ponti, et al. Isolation and in vitro propagation of tumorigenic breast cancer cells with stem/progenitor cell properties. Cancer Res. Jul. 1, 2005;65(13):5506-11.
Punnoose, et al. Molecular biomarker analyses using circulating tumor cells. PLoS One. Sep. 8, 2010;5(9):e12517. doi: 10.1371/journal.pone.0012517.
Reya, et al. Stem cells, cancer, and cancer stem cells. Nature. Nov. 1, 2001;414(6859):105-11.
Riethdorf, et al. Detection and HER2 expression of circulating tumor cells: prospective monitoring in breast cancer patients treated in the neoadjuvant GeparQuattro trial. Clin Cancer Res. May 1, 2010;16(9):2634-45. doi: 10.1158/1078-0432.CCR-9-2042. Epub Apr. 20, 2010.
Riethdorf, et al. Detection of circulating tumor cells in peripheral blood of patients with metastatic breast cancer: a validation study of the CellSearch system. Clin Cancer Res. Feb. 1, 2007;13(3):920-8.
Schiro, et al. Continuous-flow single-molecule CE with high detection efficiency. Electrophoresis. Jul. 2007;28(14):2430-8.
Schiro, et al. High-throughput fluorescence-activated nanoscale subcellular sorter with single-molecule sensitivity. J Phys Chem B. Sep. 6, 2012;116(35):10490-5. doi: 10.1021/jp3019233. Epub May 29, 2012.
Schiro, et al. Sensitive and high-throughput isolation of rare cells from peripheral blood with ensemble-decision aliquot ranking. Angew Chem Int Ed Engl. May 7, 2012;51(19):4618-22. doi: 10.1002/anie.201108695. Epub Feb. 22, 2012.
Schubert. A three-symbol code for organized proteomes based on cyclical imaging of protein locations. Cytometry A. Jun. 2007;71(6):352-60.
Schubert, et al. Toponome mapping in prostate cancer: detection of 2000 cell surface protein clusters in a single tissue section and cell type specific annotation by using a three symbol code. J Proteome Res. Jun. 2009;8(6):2696-707. doi: 10.1021/pr800944f.
Schubert. Exploring molecular networks directly in the cell. Cytometry A. Mar. 2006;69(3):109-12.
Schubert. Multiple antigen mapping microscopy of human tissue. Advances in analytical cellular pathology. 1990; 97-98.
Sheng, et al. Aptamer-enabled efficient isolation of cancer cells from whole blood using a microfluidic device. Anal Chem. May 1, 2012;84(9):4199-206. doi: 10.1021/ac3005633. Epub Apr. 17, 2012.
Shirasaki, et al. On-chip cell sorting system using laser-induced heating of a thermoreversible gelation polymer to control flow. Anal Chem. Feb. 1, 2006;78(3):695-701.
Sieuwerts, et al. Anti-epithelial cell adhesion molecule antibodies and the detection of circulating normal-like breast tumor cells. J Natl Cancer Inst. Jan. 7, 2009;101(1):61-6. doi: 10.1093/jnci/djn419. Epub Dec. 30, 2008.

Singh, et al. MUC1: a target molecule for cancer therapy. Cancer Biol Ther. Apr. 2007;6(4):481-6.
STEEG. Tumor metastasis: mechanistic insights and clinical challenges. Nat Med. Aug. 2006;12(8):895-904.
Stott, et al. Isolation of circulating tumor cells using a microvortex-generating herringbone-chip. Proc Natl Acad Sci U S A. Oct. 26, 2010;107(43):18392-7. doi: 10.1073/pnas.1012539107. Epub Oct. 7, 2010.
Sun, et al. Double spiral microchannel for label-free tumor cell separation and enrichment. Lab Chip. Oct. 21, 2012;12(20):3952-60.
Theodoropoulos, et al. Circulating tumor cells with a putative stem cell phenotype in peripheral blood of patients with breast cancer. Cancer Lett. Feb. 1, 2010;288(1):99-106. doi: 10.1016/j.canlet.2009.06.027. Epub Jul. 19, 2009.
"TW 103123208 Office Action dated Jan. 23, 2018".
"Supplementary European search report and opinion dated Mar. 24, 2017 for EP Application No. 14819852.6".
Yagublu, et al. Review: Fluorescent protein-based tumor models. In Vivo. Jul.-Aug. 2012;26(4):599-607. Review.
U.S. Appl. No. 14/903,012 Office Action dated May 22, 2018.
Vona, et al. Isolation by size of epithelial tumor cells : a new method for the immunomorphological and molecular characterization of circulatingtumor cells. Am J Pathol. Jan. 2000;156(1):57-63.
Wang, et al. Highly efficient capture of circulating tumor cells by using nanostructured silicon substrates with integrated chaotic micromixers. Angew Chem Int Ed Engl. Mar. 21, 2011;50(13):3084-8. doi: 10.1002/anie.201005853. Epub Mar. 4, 2011.
Xu, et al. A cancer detection platform which measures telomerase activity from live circulating tumor cells captured on a microfilter. Cancer Res. Aug. 15, 2010;70(16):6420-6. doi: 10.1158/0008-5472.CAN-10-0686. Epub Jul. 27, 2010.
Allen, et al. Pressure-driven laminar flow switching for rapid exchange of solution environment around surface adhered biological particles. Lab Chip. Mar. 21, 2010;10(6):727-33. doi: 10.1039/b919639k. Epub Jan. 4, 2010.
Office action dated Jan. 30, 2019 for U.S. Appl. No. 14/903,012.
Office action dated Jan. 22, 2019 for EP Application No. 17187038.9.
Office action dated Jan. 21, 2019 for JP Application No. 2017-018205.
Office action dated Jan. 29, 2014 for U.S. Appl. No. 13/257,571.
Office action dated Jan. 29, 2019 for U.S. Appl. No. 13/257,571.
"Office action dated Mar. 23, 2017 for U.S. Appl. No. 13/257,571.".
Office action dated Jun. 4, 2015 for U.S. Appl. No. 13/257,571.
"Office action dated Jun. 29, 2017 for U.S. Appl. No. 13/257,571".
Office action dated Jul. 12, 2016 for U.S. Appl. No. 13/257,571.
Office action dated Jul. 30, 2018 for U.S. Appl. No. 13/257,571.
Office action dated Sep. 11, 2014 for U.S. Appl. No. 13/257,571.
Office action dated Dec. 9, 2015 for U.S. Appl. No. 13/257,571.
"U.S. Appl. No. 13/257,571 Office Action dated Feb. 13, 2018".

* cited by examiner

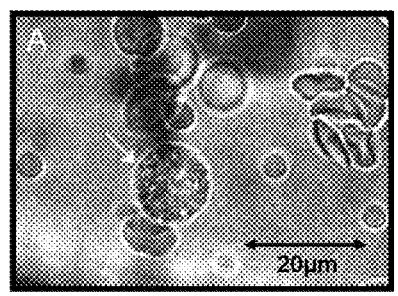 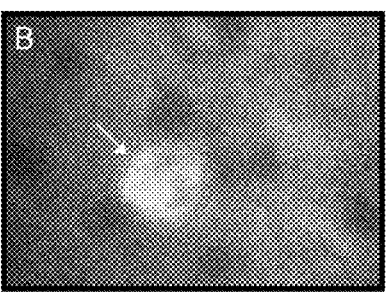 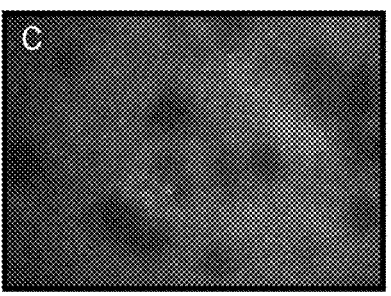
*FIG 9A*  *FIG 9B*  *FIG 9C*

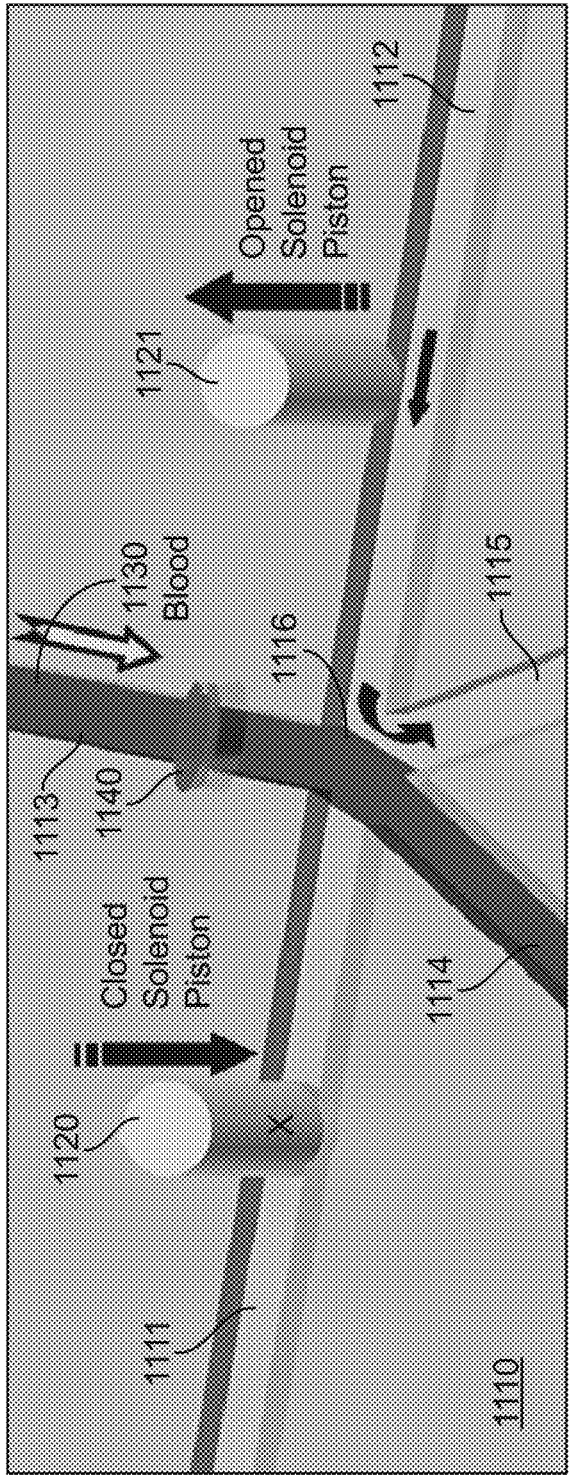
FIG. 11A
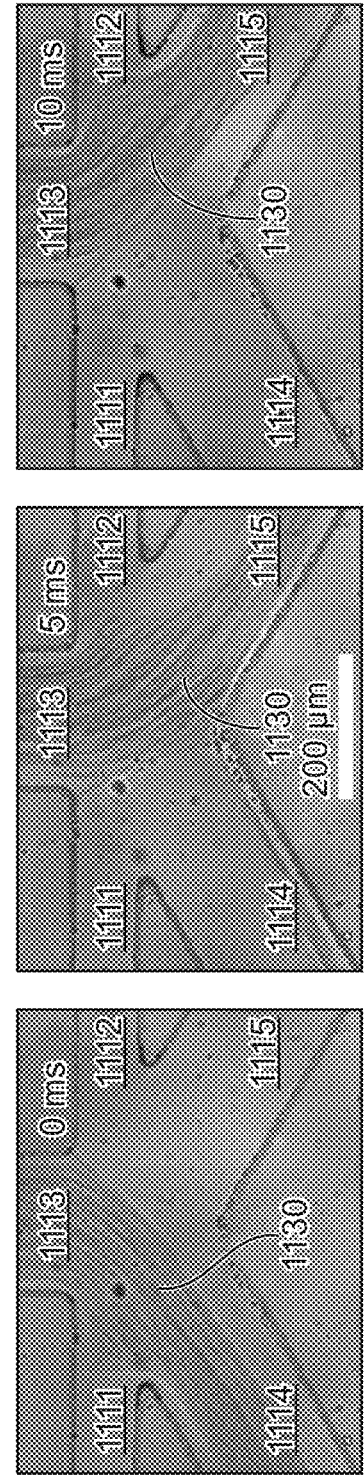
FIG. 11B
FIG. 11C
FIG. 11D

ENSEMBLE-DECISION ALIQUOT RANKING

CROSS-REFERENCES TO RELATED APPLICATIONS

The present application is a divisional application of U.S. application Ser. No. 13/257,571, filed Feb. 1, 2012, which is a U.S. National Phase Application under 35 U.S.C. § 371 of International Application No. PCT/US2010/030938, filed on Apr. 13, 2010, which claims the benefit of U.S. Provisional Application No. 61/168,892, filed Apr. 13, 2009, expressly incorporated herein by reference in their entirety for all purposes.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Body fluids are complex suspensions of biological particles in liquid. Blood, for example, includes plasma and cells (red blood cells, white blood cells, platelets) and the cells occupy about 55% of blood. Plasma is mostly water and it transfers proteins, ions, vitamins, enzymes, hormones, and other chemicals to cells in the body.

Red blood cells are about 6 to 8 µm in size and serve to provide oxygen to cells. White blood cells are about 10 to 13 µm in diameter and they defend the body from disease as a part of an immune system by fighting against foreign viruses and bacteria. Platelets are the smallest cells, 1.5 to 3 µm, and they stop bleeding by forming blood clots.

Fluids in addition to blood, such as saliva, tear, urine, cerebral spinal fluid as well as other body fluids in contact with various organs (e.g. lung) contain mixtures of cells and bioparticles. The type and amount of cells and bioparticles that are present in a particular body fluid (e.g. blood) reveals information about the health of the organism, and in the case of an infected individual, information about the diagnosis and prognosis of the disease.

Some cells or bioparticles are present in rare quantities compared to the nominal concentrations of blood cells. Despite their rare occurrence, these cells or bioparticles may be intricately tied to significant events that take place in the body that alter the health state of an individual. These cells are commonly referred to as "rare cells".

For example, dissemination of cancer cells from the primary tumor is an important factor governing the probability of relapse and the survival rate in cancer patients. As cancer cells grow unregulated and lose their ability to adhere to each other, they can enter the blood and lymphatic circulation and circulate throughout the body. These cells are commonly referred to as Circulating Tumor Cells (CTC), Disseminated Tumor Cells (DTC), Circulating Cancer Cells (CCC), Circulating Epithelial Cells (CEC), Occult Tumor Cells (OTC), or other similar permutations to indicate the mobile nature of these cells, in contrast to the specimens obtained by direct biopsy of solid tumors. CTCs have been detected in the blood of patients suffering from all major cancers: prostate, ovarian, breast, gastric, colorectal, renal, lung, pancreatic, and others.

In this fashion, tests that counts CTCs present in bodily fluids have been developed to assist with providing a prognosis for cancer patients. A "CTC test" can also be used to monitor a patient's response to a particular treatment (e.g. radiation or chemotherapy) protocol. Based on the results of CTC test, a cancer patient may be able to avoid significant costs by minimizing additional unnecessary and expensive diagnostic tests and therapies, which are often times not covered by health insurance, for example Computed Tomography (CT) or Positron Emission Tomography (PET) scans, or shorten the drug treatments that are ineffective.

However, CTCs are present in extremely low concentration in the peripheral blood, estimated to be on the order of one tumor cell per $10^6$ to $10^7$ mononuclear cells, which is equivalent to one tumor cell per 0.5 ml to 5 ml of peripheral blood. At such a low concentration, a sample with estimated 100 million mononuclear cells must be screened in order to detect at least one CTC with 99.995% certainty. Using conventional techniques, such as automatic digital microscopy (ADM) scanning at a typical speed of 800 cells/second, would require 18 hours to complete a sample that size, rendering it monetarily and temporally impractical for clinical use.

For example, conventional flow cytometry may be employed to determine the presence or quantity of CTCs in a blood sample. However, flow cytometry requires that the cells are organized linearly in a row and detect each cell singularly because simultaneous detection of two cells cannot be interpreted correctly using existing technology. In flow cytometry, laser beams are focused such that they only illuminate a single particle at any given time. For example, if one nonfluorescent cell traverses the detection volume simultaneously with a fluorescent cell configured to be detectable by the flow cytometer, the nonfluorescent cell, being invisible to the flow cytometer, would be directed in the same trajectory as the fluorescent cell. To avoid misinterpretation in flow cytometry, cells suspensions are routinely either diluted or slowed down to allow sufficient distance between the cells to avoid overlapping of two cells within the detection volume. Current state-of-the-art flow cytometers have an upper limit of sorting 100,000 objects/second.

As such, flow cytometry is not suitable for detecting or recovering rare cells. Detecting cells one at a time (serially) and making a decision on the trajectory of every cell is too time-consuming when analyzing a large number of cells. For example, since ten milliliter of blood contains approximately ten billion cells, at 100,000 cells per second, which is the highest sorting speed of state-of-the-art flow cytometer, it would take 100,000 second or 28 hours to completely sort the content of 10 mL. For rare cell, often 7-15 mL of blood is required to collect a statistically significant number of rare cells; using a flow cytometer to recover rare cells is an impractical consumption of clinical resources and can translate to a very high testing cost.

As such, simple and cost/time-effective techniques are needed for the detection and quantitation of rare particles and cells in a fluid sample. The present invention satisfies these and other needs by providing methods and apparatuses for the detection of rare particles in fluid samples.

BRIEF SUMMARY OF THE INVENTION

Among other aspects, the present invention provides methods and apparatuses that rapidly scan a large volume of a fluid for the detection and or quantitation of desired bioparticles by ranking aliquots. In one aspect, the concept employed, termed Ensemble-Decision Aliquot Ranking ("eDAR"), is particularly useful for detecting rare cells in biofluids.

In one aspect, the present invention provides a method for detecting a rare particle in a fluid sample, the method comprising the steps of detecting the presence or absence of the rare particle in an aliquot of the fluid sample, assigning a value to the aliquot based on the presence or absence of the rare particle, and directing the flow or collection of the aliquot based on the assigned value.

In a second embodiment, the present invention provides a method for providing a subject a diagnosis or prognosis for a condition associated with the presence of a rare particle in a biological fluid, the method comprising the steps of detecting the presence or absence of the rare particle in an aliquot of the biological fluid, assigning a value to the aliquot based on the presence or absence of the rare particle, and providing a diagnosis or prognosis to the subject based on the assigned value.

In a third aspect, the present invention provides a device for detecting a rare particle in a fluid sample, the device comprising at least a first input channel, at least two exit channels, at least one detector capable of detecting one or more rare particles in an aliquot of the fluid sample, a mechanism for directing the flow of the aliquot, and a computer capable of assigning a value to the aliquot based on the presence, absence, identity, composition, or quantity of the rare particles in the aliquot, wherein the computer is in communication with the detector and the mechanism for directing the flow of the aliquot.

BRIEF DESCRIPTION OF THE DRAWINGS

FIGS. 9A-9C shows the optical images of cancer cells trapped from patient blood using eDAR (arrows mark CTCs) under various illumination. FIG. 9A is a brightfield image of a CTC amidst red blood cells. FIG. 9B is a fluorescence image indicating the presence of pan-cytokeratin. FIG. 9C is a fluorescence image indicating the absence of CD45, hence ruling out the possibility of false-identifying a white blood cell as a CTC.

FIG. 10A is a fluorescence image (500-540 nm) for detecting Alexa 488-anti-CD44 (green); FIG. 10B is a fluorescence image (645-700 nm) for detecting Alexa 647-anti-CD24 (red); FIG. 10C is the brightfield image. FIG. 10D is a composite image indicating CD44+/CD24− (arrows indicate cancer stem cells).

FIGS. 11A-11D illustrate the operation of device 1110 for aliquoting a suspension.

DETAILED DESCRIPTION OF THE INVENTION

I. Overview

Figure 1:
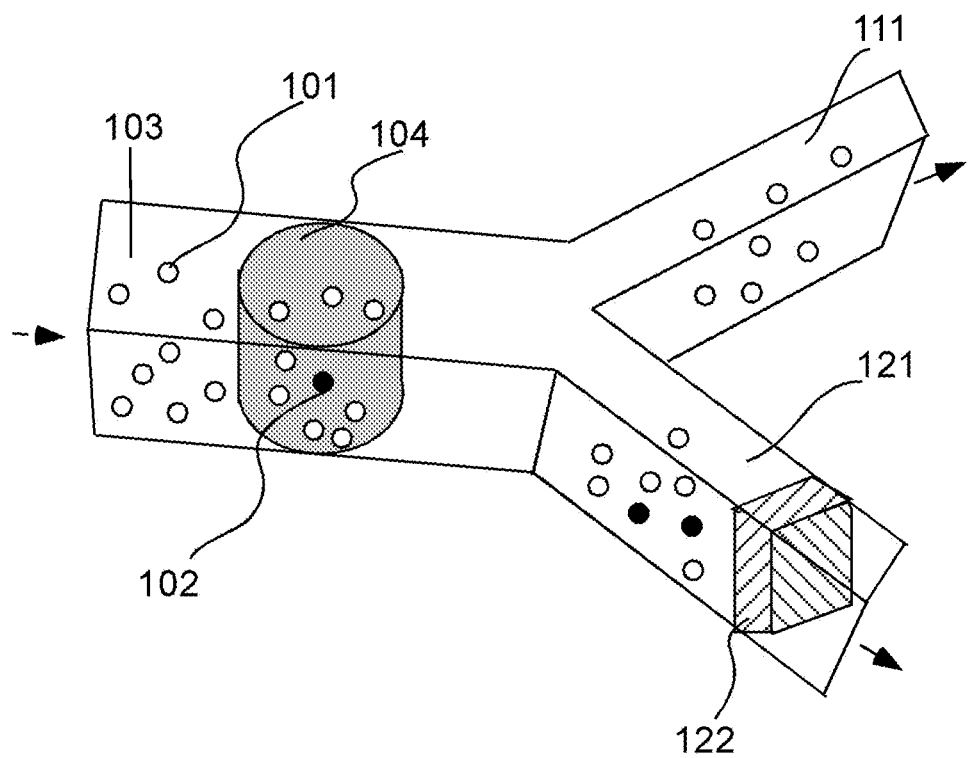
FIG. 1 illustrates simultaneous detection of multiple particles in an aliquot and the directions of aliquot.

In one aspect, the present invention provides methods and apparatuses for detecting and/or recovering rare particles in a fluid sample. The concept embodied in this aspect is referred to herein as "Ensemble-Decision Aliquot Ranking" or "eDAR." In one embodiment, the eDAR methodology can be characterized as (i) detecting the presence of absence of a rare particle in an aliquot of the fluid sample, (ii) ranking the aliquot according to the presence or absence of a rare particle, and (iii) directing the flow or collection of the entire aliquot based on the assigned ranking.

For finding rare cells, eDAR offers a tremendous advantage in speed. As an example of this, consider a 10-mL cell suspension containing 10 desired rare cells. In this case, about 99.9999% of the suspension volume does not contain a single desired rare cell. Existing technologies, such as flow cytometry, FACS, etc., invariably scan serially through every cell contained within the entire suspension volume, resulting in nearly all of time wasted scanning through the 99.9999% of the suspension volume that does not contain a desired cell. eDAR allows a quick high-level screening of the entire suspension by aliquoting the suspension. If the cells are indeed rare, most aliquots will not contain any desired cells. In one embodiment, these aliquots are ranked as null and discarded through a first channel. In comparison, the few aliquots that do contain rare cells are ranked as nonzero and collected in a separate channel or chamber.

In this fashion, eDAR is distinct from conventional flow cytometry. Flow cytometry operates by (1) flowing bioparticles in single file (i.e., one by one in a row) through the use of a sheath flow to contain the particle-row, (2) detecting only one bioparticle at a time, and (3) determine the trajectory of the bioparticle detected. If the detected bioparticle is desired, for example, the bioparticle is directed, through a one of a variety of methods, to follow a certain trajectory to reach a collection container. If the detected bioparticle is undesirable, the bioparticle is directed in a different trajectory to reach a different collection container.

In contrast to conventional flow cytometry, eDAR interrogates entire aliquots, i.e., three-dimensional subdivisions of a fluid, to make an ensemble decision for the entire aliquot. Unlike serializing (1-D subdivision of fluid, which results in bioparticles arranged in a single row) or planarizing (2-D subdivision of fluid, which results in bioparticles arranged in multiple parallel rows in a plane), aliquoting offers a much higher throughput. Flow cytometry is incapable of analyzing an aliquot because the detectors are configured only collect signals from a single cell or a single plane of cells. Bioparticles outside of the detection point or plane are entirely invisible to the detectors used in flow cytometers and consequently sheath flow, guiding buffers, or other hydrodynamic or geometric focusing mechanisms are necessary to prevent migration of bioparticles outside of the detection point or plane. eDAR analyzes an entire aliquot which spans more than one plane or layer of bioparticles. In eDAR, signals emanating from an entire aliquot, as opposed to a single detection point or plane, are analyzed.

eDAR offers significantly increased sensitivity over existing methods to detect or isolate rare cells. The detection components of eDAR can detect a single photon emanated within the entire aliquot and thus no bioparticle exhibiting detectable characteristic is missed. The rate of false-negative is extremely low because aliquot ranking is configured to eliminate only aliquots that are ranked to be completely devoid of desired bioparticles.

Embodiments in accordance with the present invention may be used in a wide variety of applications in biology and diagnosis of disease, including capturing cancer cells or cancer stem cells from body fluids for cancer prognosis; parasites such as *Giardia* or *Cryptosporidium* for water quality monitoring; malaria-infected erythrocytes for malaria diagnosis; lymphocytes and leucocytes for HIV monitoring; fetal cells in maternal blood for disease screening; stem cells for therapy; prion-infected cells for prion-related (e.g. mad cow) disease screening.

In addition to malaria, the present subject matter can be used for monitoring of CD4+ T-lymphocytes (CD4+ T-cells) in Human Immunodeficiency Virus (HIV) diagnostic and monitoring. The absolute CD4+ T-lymphocyte count can serve as a criterion to initiate antiretroviral therapy and opportunistic infection prophylaxis in HIV-infected patients. The reduction of CD4+ T-lymphocytes, which is a subpopulation of leucocytes (white blood cells), strongly correlates to the decline of the immunological defense. Monitoring of CD4+ T-lymphocytes (CD4+ T-cells) level every 3-6 months in all HIV-infected persons has been recommended by the CDC Public Health Service as a way to initiate appropriate treatment strategies and to evaluate treatment efficacy.

In some laboratories, the absolute CD4+ T-cell number is established using the product of three laboratory techniques: the total white blood cell count, the percentage of white blood cells that are lymphocytes, and the percentage of lymphocytes that are CD4+ T-cells. Single platform flow cytometers such as FACSCount (BD Biosciences) are commercially unavailable in developing countries or as a portable device. Embodiments according to the present subject matter can be used to rapidly distinguish CD4+ T-lymphocytes from other leucocytes and RBCs.

Additional possible applications for separation, concentration, and/or isolation addressed by embodiments in accordance with the present invention, include fetal cell monitoring in maternal blood for prenatal diagnostic of genetic disorders and prion detection. A prion includes a small infectious proteinaceous particle which resists inactivation by procedures that modify nucleic acids. In addition, embodiments according to the present subject matter can be used with fetal cells or other micro-biological particulates or nano-biological particulates.

II. Definitions

As used herein, a "fluid sample" refers to any liquid that may or may not contain a rare particle of interest. In certain embodiments, the fluid sample may be a biological fluid sample, for example a blood sample, plasma sample, saliva sample, urine sample, lymph sample, spinal fluid sample, and the like. In other embodiments, the sample may be an environmental fluid sample, for example from a lake, river, ocean, pond, stream, spring, marsh, reservoir, or the like. In yet other embodiments, the sample may be a water sample, for example from a desalinization plant, water treatment plant, reservoir, spring, stream, glacial water flow, water tower, or other water source that may be contemplated as a source of potable water.

As used herein, a "rare particle" refers to a cell or macromolecule present in a fluid sample at a low level. In certain embodiments, a rare particle may be a cell, protein, protein complex, nucleic acid, nucleoprotein complex, carbohydrate, metabolite, catabolite, and the like. In certain embodiments, a particle may be considered rare if it is present in a fluid sample at a concentration of less than about 10% of the total particle population in the fluid, or at less than about 9%, 8%, 7%, 6%, 5%, 4%, 3%, 2%, 1%, 0.5%, 0.1%, 0.05%, 0.01%, or less of the total particle population in the fluid. In yet other embodiments, the rare particle may be present in a fluid sample at less than about 1 part per $10^3$ of the total particle population in the fluid, or at less than about 1 part per $10^4$, $10^5$, $10^6$, $10^7$, $10^8$, $10^9$, $10^{10}$, $10^{11}$, $10^{12}$, or less of the total particle population in the fluid.

In a particular embodiment, the rare particle is a rare cell. Rare cells may be nucleated or non-nucleated. Rare cells include, but are not limited to, cells expressing a malignant phenotype; fetal cells, such as fetal cells in maternal peripheral blood; tumor cells, such as tumor cells which have been shed from tumor into blood or other bodily fluids; cells infected with a virus, such as cells infected by HIV, cells transfected with a gene of interest; and aberrant subtypes of T-cells or B-cells present in the peripheral blood of subjects afflicted with autoreactive disorders.

As used herein, an "ensemble-decision" refers to a decision made based on the detection of the presence or absence of a characteristic in an ensemble, or a group, of particles. In certain embodiments, an ensemble-decision will be made based on the presence or absence of a single distinct particle in an aliquot of a fluid sample containing a plurality of particles. Importantly, ensemble-decisions made based on the presence or absence of a single particle will be applied to the entire aliquot (i.e., to all of the particles present in the aliquot).

As used herein, an "aliquot" refers to a portion of the total volume of a fluid sample to be analyzed. An aliquot occupies a three-dimensional space and the particles within distribute randomly without organization. An aliquot has a finite depth, and particles may distribute along the depth with no discernible layers. In the context of the present invention, an aliquot is analyzed in its entirety without sub-division. Sheet, ribbon, plane or similar terms suggesting two-dimensional spaces and used to describe current cell sorting methods (e.g., flow cytometry, FACS, etc.) that typically employ hydrodynamic focusing are not considered an aliquot.

In certain embodiments, an aliquot may consist of a fraction of a larger fluid sample, for example, about ½ of a fluid sample, or about ⅓, ¼, ⅕, ⅙, ⅐, ⅛, ⅑, ⅒, or less of a fluid sample. In certain embodiments, an aliquot may consist of, for example, about 10% of a fluid sample, or about 9%, 8%, 7%, 6%, 5%, 4%, 3%, 2%, 1%, 0.5%, 0.1%, 0.05%, 0.01%, 0.001%, or less of a fluid sample. As such, a fluid that is to be examined or processed by an eDAR methodology provided herein may be divided, for example, into at least about 2 aliquots, or at least about 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 175, 200, 225, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, 3,000, 3,500, 4,000, 4,500, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1 million, 2 million, 3 million, 4 million, 5 million, 6 million, 7 million, 8 million, 9 million, 10 million, or more aliquots. One of skill in the art would understand that the number of aliquots into which a fluid sample would be partitioned into will depend upon the number of rare particles expected in the fluid and the total volume of the fluid sample.

In certain embodiments, an aliquot may have a volume, for example, of between about 0.1 nL and about 10 mL, or between about 1 nL and about 1 mL, or between about 1 nL and about 100 µL, or between about 1 nL and about 10 µL, or between about 1 nL and about 1 µL, or between about 1 nL and about 100 nL.

As used herein, the term "ranking" refers to assessing a quantitative property, qualitative property, or importance of an aliquot by categorization. In one embodiment, an aliquot may be ranked as either null (for example, when a rare particle is not detected in the aliquot) or nonzero (for example, when at least one rare particle is detected in an aliquot). In one embodiment, the ranking may be binary. In other embodiments, an aliquot may be ranked according to additional categories, for example, which correlate with the concentration of the rare particle in the aliquot, the identity of the rare particle in the aliquot, the identities of a plurality of different rare particles in the aliquot, and the like. In this fashion, any number of categories may be assigned based on ranges of concentration, for example, between about 1 and 10, between about 11 and 20, between about 1 and 50, between about 51 and 100, between about 1 and 100, between about 101 and 201, etc. These rankings may be assigned an arbitrary number corresponding to one of a number of predetermined quantitative or qualitative categories (e.g., 0, 1, 2, 3, 4, 5, etc.), or a number corresponding to an actual value for the number or approximate number or rare particles in the aliquot.

As used herein, a "detectable characteristic" refers to a property associated with a rare particle, for example, a photoactive, electroactive, bioactive, or magnetic property that is intrinsic to the rare particle or which is associated with a detectable moiety bound to or conjugated to the rare particle.

Examples of photoactive properties include, for example, alterations in optical intensity (optical reflection, scattering, deflection, transmission, or absorbance) commonly induced by bioparticle morphology (particle size, granularity, internal subcellular structures), fluorescence, immunofluorescence, and the like.

Examples of electroactive properties include, for example, changes in the electrical charge, oxidation state, spin state, capacitance, conductance, dielectric properties, electrophoretic mobility, or polarizability.

Examples of bioactive properties include, for example, detectable interactions with enzymes such as alkaline phosphatase (AP), horseradish peroxidase (HRP), β-Galactosidase and their chemiluminescent, colometric, or chemifluorescent substrates, which include but are not limited to TMB (3,3',5,5'-Tetramethylbenzidine), OPD (o-phenylene Diamine, ABTS (2,2'-azinodiethylbenzthiazoline sulfonate), chlornaphthol, AEC (3-amino-9-ethylcarbazole), DAB (Di-aminobenzidine), pNPP (p-Nitrophenyl Phosphate), BCIP/NBT (Bromochloroindolyl Phosphate-Nitro blue Tetrazolium, and the like.

In certain embodiments, moieties that can be used to detect a rare particle include, without limitation, nanoparticles, microbeads, antibodies and fragments thereof, fluorescent antibodies, magnetic nanoparticles, polymer molecules, dye molecules, DNA or RNA molecules (e.g. aptamers), lipid molecules, protein molecules, and the like.

As used herein an "antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature*, 348:552-554 (1990)).

In one embodiment, the antibody is conjugated to a label or detectable moiety.

As used herein, a "label" or a "detectable moiety" refers to a composition detectable by spectroscopic, photochemical, biochemical, immunochemical, chemical, or other physical means. For example, useful labels include, without limitation radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

In certain embodiments, detection reagents may be perfused to selectively label or accentuate the isolated cells. Examples of such reagents include, without limitation, fluorescent, immunofluorescent, dye-conjugated molecules (such as antibodies, fab fragments, aptamers, polymers, ligands, agonists, antagonists, or combinations thereof) magnetic, electroactive, bioactive, or photoactive compounds. An example is to use a stain that reacts with cytokeratins, which are integral components of the cytoskeleton in epithelial cancerous cells. Other dye examples include fluorescein isothiocyanate (FITC)-conjugated mouse anti-human epithelial antibody (HEA) and phycoerythrin (PE)-conjugated anti-CD45. Other examples of dye-conjugated antibodies include but are not limited to the pan-cytokeratin antibody A45B/B3, AE1/AE3, or CAM5.2 (pan-cytokeratin antibodies that recognize Cytokeratin 8 (CK8), Cytokeratin 18 (CK18), or Cytokeratin 19 (CK19) and ones against: breast cancer antigen NY-BR-1 (also known as B726P, ANKRD30A, Ankyrin repeat domain 30A); B305D isoform A or C (B305D-A ro B305D-C; also known as antigen B305D); Hermes antigen (also known as Antigen CD44, PGP1); E-cadherin (also known as Uvomorulin, Cadherin-1, CDH1); Carcino-embryonic antigen (CEA; also known as CEACAM5 or Carcino-embryonic antigen-related cell adhesion molecule 5); β-Human chorionic gonadotophin (β-HCG; also known as CGB, Chronic gonadotrophin, β polypeptide); Cathepsin-D (also known as CTSD); Neuropeptide Y receptor Y3 (also known as NPY3R; Lipopolysaccharide-associated protein3, LAP3, Fusion; Chemokine (CXC motif, receptor 4); CXCR4); Oncogene ERBB1 (also known as c-erbB-1, Epidermal growth factor receptor, EGFR); Her-2 Neu (also known as c-erbB-2 or ERBB2); GABA receptor A, pi ($\pi$) polypeptide (also known as GABARAP, GABA-A receptor, pi ($\pi$) polypeptide (GABA A($\pi$), γ-Aminobutyric acid type A receptor pi ($\pi$) subunit), or GABRP); ppGalNac-T(6) (also known as β-1-4-N-acetyl-galactosaminyl-transferase 6, GalNActransferase 6, GalNAcT6, UDP-N-acetyl-d-galactosamine: polypeptide N-acetylgalactosaminyltransferase 6, or GALNT6); CK7 (also known as Cytokeratin 7, Sarcolectin, SCL, Keratin 7, or KRT7); CK8 (also known as Cytokeratin 8, Keratin 8, or KRT8); CK18 (also known as Cytokeratin 18, Keratin 18, or KRT18); CK19 (also known as Cytokeratin 19, Keratin 19, or KRT19); CK20 (also known as Cytokeratin 20, Keratin 20, or KRT20); Mage (also known as Melanoma antigen family A subtypes or MAGE-A subtypes); Mage3 (also known as Melanoma antigen family A 3, or MAGA3); Hepatocyte growth factor receptor (also known as HGFR, Renal cell carninoma papillary 2, RCCP2, Protooncogene met, or MET); Mucin-1 (also known as MUC1, Carcinoma Antigen 15.3, (CA15.3), Carcinoma Antigen 27.29 (CA 27.29); CD227 antigen, Episialin, Epithelial Membrane Antigen (EMA), Polymorphic Epithelial Mucin (PEM), Peanut-reactive urinary mucin (PUM), Tumor-associated glycoprotein 12 (TAG12)); Gross Cystic Disease Fluid Protein (also known as GCDFP-15, Prolactin-induced protein, PIP); Urokinase receptor (also known as uPR, CD87 antigen, Plasminogen activator receptor urokinase-type, PLAUR); PTHrP (parathyrold hormone-related proteins; also known as PTHLH); BS106 (also known as B511S, small breast epithelial mucin, or SBEM); Prostatein-like Lipophilin B (LPB, LPHB; also known as Antigen BU101, Secretoglobin family 1-D member 2, SCGB1-D2); Mammaglobin 2 (MGB2; also known as Mammaglobin B, MGBB, Lacryglobin (LGB) Lipophilin C (LPC, LPHC), Secretoglobin family 2A member 1, or SCGB2A1); Mammaglobin (MGB; also known as Mammaglobin 1, MGB1, Mammaglobin A, MGBA, Secretoglobin family 2A member 2, or SCGB2A2); Mammary serine protease inhibitor (Maspin, also known as Serine (or cystein) proteinase inhibitor clade B (ovalbumin) member 5, or SERPINB5); Prostate epithelium-specific Ets transcription factor (PDEF; also known as Sterile alpha motif pointed domain-containing ets transcription factor, or SPDEF); Tumor-associated calcium signal transducer 1 (also known as Colorectal carcinoma antigen CO17-1A, Epithelial Glycoprotein 2 (EGP2), Epithelial glycoprotein 40 kDa (EGP40), Epithelial Cell Adhesion Molecule (Ep-CAM), Epithelial-specific antigen (ESA), Gastrointestinal tumor-associated antigen 733-2 (GA733-2), KS1/4 antigen, Membrane component of chromosome 4 surface marker 1 (M4S1), MK-1 antigen, MIC18 antigen, TROP-1 antigen, or TACSTD1); Telomerase reverse transcriptase (also known as Telomerase catalytic subunit, or TERT); Trefoil Factor 1 (also known as Breast Cancer Estrogen-Inducible Sequence, BCEI, Gastrointestinal Trefoil Protein, GTF, pS2 protein, or TFF1); folate; or Trefoil Factor 3 (also known as Intestinal Trefoil Factor, ITF, p1.B; or TFF3).

The phrase "specifically (or selectively) binds" to an antibody or "specifically (or selectively) immunoreactive with," when referring to a rare particle, for example a protein, nucleic acid, or cell, refers to a binding reaction that is determinative of the presence of the rare particle, often in a heterogeneous population of particles and other biologics. Thus, under designated immunoassay conditions, the specified antibodies bind to a particular rare particle at least two times the background and more typically more than 10 to 100 times background. Specific binding to an antibody under such conditions requires an antibody that is selected for its specificity for a particular particle. For example, polyclonal antibodies can be selected to obtain only those polyclonal antibodies that are specifically immunoreactive with the selected antigen and not with other proteins. This selection may be achieved by subtracting out antibodies that cross-react with other molecules.

In one aspect, the present invention provides a method for detecting one or more rare bioparticles in a sample fluid; said method comprising: a) interrogating one or more aliquots of said sample fluid; b) in a single measurement detecting presence or absence of said one or more rare bioparticles in each of said one or more aliquots wherein at least one of said one or more aliquots comprises multiple bioparticles; and c) ranking said aliquots based on the presence or absence of said one or more rare bioparticles. In certain embodiments, the rare bioparticles are cells. In a certain embodiment, the rare bioparticles are fluorescent labeled cells.

In some embodiments of the methods provided herein, multiple parameters are detected in a single measurement. In a particular embodiment, the multiple parameters are different fluorescent colors.

In certain embodiments of the methods provided herein, the sample fluid is stabilized by addition of anticoagulants, compounds that prevent agglomeration of cells in the sample including said bioparticles or their combinations.

In some embodiments, the aliquot ranking is binary, for example an aliquot is assigned a value of "0" if the aliquot does not contain a rare article and a value of "1" if it does. In other embodiments, the ranking is non-binary, for example, the value is assigned based on the number or rare particles present in the aliquot or the identity of the rare particles in the sample. In certain embodiments, the ranking is performed by a computer and a software representing a ranking algorithm.

In some embodiments, the methods provided herein further comprise a step of channeling the aliquots based on their ranking. For example, the flow or collection of the aliquots is directed based on the value assigned to the aliquot. In certain embodiments, this is achieved by the use of external fields or by creating flow disturbances.

In certain embodiments, the method may comprise concentrating the rare bioparticles by collecting and/or pooling aliquots with similar said ranking.

In some embodiments, of the methods provided herein, the rare bioparticles are selected from the group consisting of cancer cells, cancer stem cells, *Giardia, Cryptosporium*, malaria infected erythrocytes, lymphocytes, leucocytes, fetal cells, stem cells and prion-infected cells.

In another aspect, the present invention provides a device for detecting one or more rare bioparticles in a sample fluid; said device comprising: a) one or more detectors for detecting presence or absence of one or more rare bioparticles in each of the one or more aliquots wherein at least one of said one or more aliquots comprises multiple bioparticles; and b) a computer with software for ranking said aliquots based on presence or absence of said one or more rare bioparticles. In one embodiment, the ranking is binary. In other embodiments, wherein the device is used to detect multiple types of bioparticles, the ranking is non-binary.

In certain embodiments, the device may further comprise channels for channeling said aliquots based on said ranking. In particular embodiments, the channels are treated with anticoagulant compounds, compounds that preferentially bind to the rare bioparticles, compounds that prevent bioparticles agglomeration or their combinations.

In certain embodiments, the device may further comprise electrodes for tracking and manipulating the trajectory of said bioparticles. In other embodiments, the device may further comprise magnetic elements for the separation of bioparticles with attached magnetic particles. In et other embodiments, the device may further comprise acoustical elements for tracking and manipulating the trajectory of said bioparticles.

In certain embodiments of the devices and apparatuses provided herein, the device comprises one or more detectors are selected from a camera, an electron multiplier, a charge-coupled device (CCD) image sensor, a photomultiplier tube (PMT), an avalanche photodiode (APD), a single-photon avalanche diode (SPAD), or a complementary metal oxide semiconductor (CMOS) image sensor.

In certain embodiments of the devices and apparatuses provided herein, the device may further comprise one or more sources for interrogating one or more aliquots of said sample fluid. For example, a source of electromagnetic radiation. In particular embodiments, the one or more sources for interrogating are selected from, a laser (solid state, diode-pumped, ion, or dye), a light-emitting diode (LED), a lamp, an arc discharge, a magnetic pulse, or a natural light. In yet other embodiments, a source for interrogation of the aliquot is not required when the bioparticle exhibits light emission such as chemiluminescence or bioluminescence.

III. Embodiments

A. Detection Methods

In one aspect, the present invention provides a method for detecting a rare particle in a fluid sample, the method comprising the steps of: (a) detecting the presence or absence of the rare particle in an aliquot of the fluid sample; (b) assigning a value to the aliquot based on the presence or absence of the rare particle; and (c) directing the flow or collection of the aliquot based on the assigned value.

In one embodiment, the step of detecting the presence of the rare particle comprises the sub-steps of: (i) contacting the fluid sample with a detection reagent under conditions suitable to transform the detection reagent into a complex comprising said detection reagent and a rare particle; and (ii) detecting the presence or absence of a complex formed in step (i) in an aliquot of the fluid sample.

In certain embodiments, the detection reagent may comprise a labeled or unlabeled antibody, fab fragment, aptamer, polymer, nanoparticle, microbead, fluorescent antibody, magnetic nanoparticle, polymer molecule, dye molecule, aptamer, lipid molecule, protein molecule, and the like.

In another embodiment, the step of detecting the presence of the rare particle comprises the sub-steps of: (i) interrogating the aliquot with an external source of electromagnetic radiation; and (ii) detecting fluorescence of the rare particle.

In one embodiment, the rare particle may comprise a fluorescently labeled cell. In a certain embodiment, the fluorescently labeled cell may comprise a cell that expresses a fluorescent protein, or a cell that has been labeled with a fluorescent detection reagent. For example, a cell that transiently or stably expresses a red or green fluorescent protein.

In yet another embodiment, wherein the rare particle exhibits intrinsic chemiluminescence or bioluminescence, the step of detecting the presence of a rare particle comprises detecting bioluminescence or chemiluminescence of the rare particle.

In certain embodiments, the rare particle may be a cell, protein, protein complex, nucleic acid, nucleoprotein complex, carbohydrate, metabolite, catabolite, and the like. In one embodiment, the rare particle is a cell. In particular embodiments, the cell may be a cancer cell, a circulating tumor cell (CTC), a cancer stem cell, a cancer cell displaying a cancer surface antigen, for example, one selected from the groups consisting of CD44, CD2, CD3, CD10, CD14, CD16, CD24. CD31, CD45, CD64, CD140b, or a combination thereof.

Cancer stem cells may be distinguished from ordinary cancer cells by perfusing other reagents that selectively bind to biomarkers, which may include but are not limited to CD44, CD2, CD3, CD10, CD14, CD16, CD24. CD31, CD45, CD64 or CD140b.

In certain embodiments, wherein the rare particle is a cancer cell, cells contained within the aliquots identified as having a rare cell may be further individually dissected. For example, these cells may be further partitioned or sorted via traditional flow cytometry or eDAR and desired cells may be dissected to understand the origin of malfunctioning cellular machinery. The contents within each cell may be individually analyzed for DNA, RNA, DNA sequence, metabolite, lipid, carbohydrate, protein content, or the like.

In other embodiments, the rare cell may be a parasitic cell or organism, for example, a species of *Giardia* or *Cryptosporidium*, a erythrocyte infected with a species of *Plasmodium*, a lymphocyte or leucocyte infected with HIV, a fetal cell in maternal blood, a stem cell, a prion-infected cell, a CD4+ T-cell, and the like.

In one embodiments, the fluid sample may comprise more than one type of rare particle, for example, 2, 3, 4, 5, 6, 7, 8, 9, 10 or more types of rare particles. Accordingly, in certain embodiments, the fluid sample is simultaneously contacted with a plurality of differentiable detection reagents each having a different specificity under conditions sufficient to transform the plurality of detection reagents into a plurality of complexes comprising the detection reagents and a plurality of rare particles. In some embodiments, the plurality of complexes are detected simultaneously, for example, by using an eDAR apparatus that comprises more than one interrogation devices and/or more than one detection devices.

For example, in the case that two rare particles are to be detected simultaneously, each rare particle may be contacted with a differentiable detection reagent, each of which may be detected by one of two detection devices. Furthermore, wherein the detection reagents comprise fluorescent moieties, two interrogation devices (e.g., two lasers producing radiation at different wavelengths corresponding to excitation wavelengths of the different fluorescent moieties) may be used and the respective fluorescent radiation may be detected by two different detection devices. Accordingly, in one embodiment, the detection reagents are differentiable by fluorescence at different wavelengths.

In yet another embodiment, the two or more rare particles may be detected in series. For example, in one embodiment, the method may comprise detecting a first rare particle at a first location of an eDAR apparatus and detecting a second rare cell at a second location of an eDAR apparatus. In this fashion, the aliquot in which the first and second particle reside may be channeled after the first detection step, after the second detection step, or after both detection steps.

In certain embodiments of the invention, detection of a characteristic from an ensemble of cells can be simultaneous or cumulative over time. For example, detection of a characteristic can emanate at once ("simultaneous") from a large aliquot containing an ensemble of bioparticles.

In certain embodiments, in which the method is performed in a simultaneous mode, the bioparticles may be carried by a flow of variable velocity. As an example, bioparticles may be carried by a steady flow as they traverse through the detection volume. Alternatively, the flow may be stopped, decelerated, or accelerated as the cells traverse through the detection volume. Flow may be regulated with one of the following either upstream or downstream of the detection volume: a valve, a bubble, an electric field, a magnetic field, an optical field, a pneumatic pressure source, a solid particle, a membrane, an immiscible droplet, a gravitational differential, or a coating to alter surface tension of the channel.

In some embodiments of the methods provided herein, the detection step is performed during continuous flow of the fluid sample through a flow channel. In certain embodiments, the individual aliquots are not physically separated, but rather are defined by the optical detection step, i.e., an aliquot may be defined as the ensemble of particles present in the detection volume at the instant the detection occurs.

In certain embodiments, the detection event will occur with a regular frequency, which is dependent upon both the size of the detection volume and the flow rate of the fluid sample. For example, if the detection volume of a particular apparatus is 10 µL and the fluid sample is flowed through the apparatus at a rate of 100 µL/second, a different aliquot will be detected every 0.1 seconds, or at a rate of 10 Hz.

In certain embodiments, dependent upon the geometry of the apparatus and the volume of the fluid to be processed, discrete aliquots traverse through the detection volume at a rate between 0.1 kHz and 100 MHz. In another embodiment, the discrete aliquots traverse through the detection volume at a rate between about 10 Hz and about 10 MHz. In other embodiments, the discrete aliquots may traverse through the detection volume at a frequency of between about 0.1 kHz and about 100 MHZ, or between about 1 kHz and about 10 MHz, or between about 1 kHz and about 5 MHz, or between about 1 kHz and about 1 MHz. In certain embodiments, the frequency by which the aliquots traverse through the detection volume may be at least about 0.1 kHz, or at least about 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 60, 70, 80, 90, 100, 125, 150, 200, 250, 300, 400, 500, 600, 700, 800, or 900 kHz, or at least about 1 MHz, or at least about 2, 3, 4, 5, 6, 7, 8, 9, 10, 15, 20, 25, 30, 35, 40, 45, 50, 60, 70, 80, 90, or 100 MHz.

In other embodiments of the methods provided herein, detection of a characteristic from an ensemble of cells can emanate over time ("cumulative") from a small detection volume which is on the order of a single cell, but with multiple cells traversing through the detection volume with the aid of flow. Cumulative mode of eDAR is distinct from time-lapse overlay of consecutive signals or frames emanating from a single bioparticle; timelapse overlay of a single bioparticle does not constitute an ensemble of bioparticles. In both simultaneous and cumulative, a decision is rendered only after a characteristic from an ensemble of cells has been detected.

In yet other embodiments of the methods provided herein, the aliquots may be physically separated prior to detection. This may be accomplished, for example, by partitioning the sample fluid into discrete aqueous aliquots separated by air or a continuous oil-immiscible fluid phase, for example, into a droplet.

In one embodiment, the immiscible phase used to separate aqueous aliquots may include an organic phase, an oil, natural oils such as mineral oil and soybean oil, silicone oils such as AR-20, AS-4, PDMS oil, fluorinated oils such as Fluorinert and perfluorodecalin, organic solvents such as hexadecane and acetophenone, a wax, air, or gas.

In certain embodiments, an immiscible phase may be continuous (i.e. surrounds the discrete aliquots entirely) or segmented (i.e. occupies only the spacing between discrete aliquots but does not completely surround the aliquots).

Figure 16:
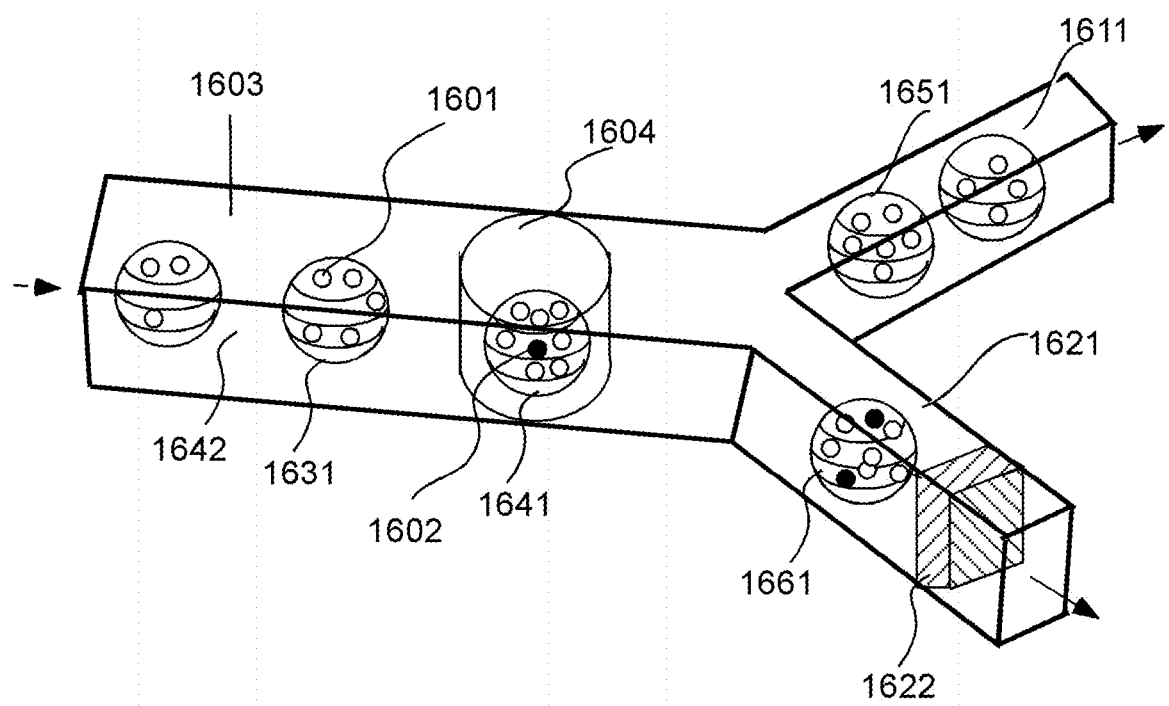
FIG. 16 illustrates the use of discrete aqueous aliquots separated by an immiscible phase to encapsulate bioparticles prior to reaching the detection volume.

For example, FIG. 16 illustrates a an immiscible phase (1642) that surrounds the discrete aliquots entirely.

In one embodiment, the discrete aliquots are droplets. In another embodiment, the discrete aliquots are plugs.

In one embodiment, the discrete aliquots may be formed sequentially on an eDAR apparatus in a flow channel in fluidic communication with the flow channel.

In certain embodiments, the discrete aliquots may be formed externally of the eDAR apparatus but flowed into a flow channel of the apparatus via a tubing, a port, or an interconnect in fluidic communication with the flow channel.

In one embodiment, surfactants may be added to the cell suspension or the immiscible phase to stabilize the discrete aliquots. Surfactants may include albumin (bovine or human serum albumin), Span 80, Pluronic, octaethylene glycol monodecyl ether, tetraethylene glycol monodecyl ether, zwitterionic surfactants such as N-dodecyl-N, N-dimethyl-3-ammonio-1-propanesulfonate (DDAPS), anionic surfactants such as sodium dioctyl sulfosuccinate (AOT), cationic surfactants such as cetyl trimethyl ammonium bromide (CTAB), and silicone-based, PEGylated and fluorinated surfactants.

In yet another embodiment, the fluid sample may be partitioned into aliquots and physically separated into separate flow channels or chambers of an eDAR apparatus prior to the detection step. The subsequent detection step may then be performed either in parallel (i.e., at the same time using multiple detection devices or a single detection device), or sequentially, for example by directing the individual aliquots sequentially through one or more detection volumes.

In some embodiments of the invention, the fluid sample, for example a biological fluid sample, may be stabilized prior to detection of a rare particle. In certain embodiments, the fluids may be stabilized with a reagents, including but not limited to, an anticoagulant such as citrate, heparin, ethylenediamine tetraacetic acid (EDTA), diethylenetriamine pentaacetic acid (DTPA), 1,2-diaminocyclohexane tetraacetic acid (DCTA), or ethylene bis(oxyethylenenitrilo) tetraacetic acid (EGTA); an aldehyde such as methylol, hydroxymethyl derivatives of amines or amides of formaldehyde, diazolinidinyl urea, imidazolidinyl urea, methenamine, paraformaldehyde, glutaraldehyde, or glyoxal, and the like.

In yet other embodiments of the invention, the methods provided herein may be further coupled to a secondary process occurring after channeling of the desired aliquots. Example of processes and/or functions that may be coupled to a method provided herein include, for example, selective reactions to identify cellular contents (e.g. DNA, RNA, microRNA, lipids, metabolites, carbohydrates, or proteins encapsulated within cells). These reactions include Polymerase Chain Reaction (PCR), Real-Time Polymerase Chain Reaction (RT-PCR), isothermal PCR, reactions to determine the epigenetic states of DNA, single-molecule hybridization reactions to determine the microRNA and siRNA contents, or aptamer (short strands of DNA)-selective reactions.

In certain embodiments, the methods provided herein may further be coupled to an assay protocol following aliquot or cell isolation. Non-limiting examples of assays that may be coupled to the methods provided herein include nucleic-acid based methods such as RNA extraction (with or without amplification), cDNA synthesis (reverse transcription), gene microarrays, DNA extraction, Polymerase Chain Reactions (PCR) (single, nested, quantitative real-time, or linker-adapter), or DNA-methylation analysis; cytometric methods such as fluorescence in situ hybridization (FISH), laser capture microdissection, flow cytometry, fluorescence activated cell sorting (FACS), cell culturing, or comparative genomic hybridization (CGH) studies; chemical assay methods such as electrophoresis, Southern blot analysis or enzyme-linked immunosorbent assay (ELISA); assays to determine the microRNA and siRNA contents; assays to determine the DNA/RNA content; assays to determine lipid contents; assays to determine carbohydrate contents; assays to determine metabolite contents; assays to determine protein contents; and functional cell assays (e.g. apoptotic assays, cell migration assays, cell proliferation assays, cell differentiation assays, etc.), and the like.

In yet another embodiment, the methods provided herein may further be coupled to flow cytometry, for example, to further partition or isolate rare particles present in a selected aliquot. In one embodiment, a channel of the eDAR device used for the methods provided herein may be in fluidic communication with a flow cytometer. In certain embodiments, the coupling of eDAR and flow cytometry allows for selected aliquots to be further examined or serially sorted to further enrich a population of rare particles or cells. In certain embodiments of the methods provided herein, this configuration allows for upstream gross-sorting of rare particles or cells and only directs aliquots containing rare particles or cells into downstream processes, such as flow cytometry, that are time, cost, and/or labor intense.

In certain embodiments, the methods provided herein may be performed using an eDAR apparatus provided herein.

1. Advantageous Features

As noted above, due in part to the ensemble detection and ranking of whole aliquots, rather than individual cells or particles, eDAR technologies are much faster and less expensive than traditional flow cytometry methods currently employed. Several features contribute to the improved eDAR methodologies.

For example, in one embodiment of the methods provided herein, an aliquot comprises more than a single particle, cell, or fluorescent entity. In this regard, discreet volumes containing a plurality of cells or particles, rather than single cells or particles, or 1 dimensional sheets of cells or particles, can be interrogated simultaneously.

In a related embodiment of the methods provided herein, the particles or cells of a fluid do not need to enter the detection spot or volume serially (i.e., one after another without overlapping presence). In a related embodiment, the particles do not need to enter the detection spot or volume in a single row or sheet. Accordingly, in one embodiment of the methods provided herein, multiple bioparticles, within a single aliquot, may pass through a cross-section or cross-sectional volume of a flow channel, for example an interrogation and/or detection volume, at a time.

In one embodiment of the methods provided herein, a sheath flow, guiding buffer, or other hydrodynamic or geometric focusing mechanisms is not needed to focus the bioparticles into a single row for interrogation and/or detection.

In one embodiment of the methods provided herein, a ranking scheme or value assignment scheme of complete aliquots is employed, instead of sorting individual bioparticles.

In one embodiment of the methods provided herein, an ensemble of particles or cells is detected simultaneously, for example as a single aliquot of a larger fluid sample. In a related embodiment, a decision made for an aliquot affects the entire ensemble of particles or cells contained within the aliquot. In yet another related embodiment, an ensemble of particles or cells detected simultaneously within an aliquot will remain as an ensemble of particles or cells.

2. Aliquot Ranking

In one embodiment of the methods provided herein, the aliquot is assigned either a first value is the aliquot contains a rare particle or a second value if the aliquot does not contain a rare particle. In a particular embodiment, the ranking (i.e., assignment of a value) is binary. For example, each aliquot containing at least one rare particle is assigned a value of 1, while each aliquot not containing a rare particle is assigned a value of 0.

In another embodiment of the methods provided herein, the aliquot is assigned a value according to the quantity of rare particles present in the aliquot. For example, an aliquot containing 4 rare particles may be assigned a value of 4. Alternatively, an aliquot containing 4 particles may be assigned a value that corresponds to a particular range of rare particle quantities, for example 0 to 5 particles, 1 to 10 particles 4 to 6 particles, etc.

In yet another embodiment of the methods provided herein, wherein more than one type of rare particles are present in a single fluid sample, an aliquot is assigned a value according to the identities of any rare particles in the aliquot. For example, wherein a fluid sample contains two rare particles, A and B, an aliquot containing neither A nor B may be assigned a value of 0, an aliquot containing only A may be assigned a value of 1, an aliquot containing only B may be assigned a value of 2, and an aliquot containing both A and B may be assigned a value of 3. Accordingly, in one embodiment of the methods provided herein, wherein more than one type of rare particles are present in a single fluid sample, the ranking (i.e., assignment of a value) is not binary.

In certain embodiments, a non-null assigned value may depends on either the identity of the rare particle or the concentration of the rare particle.

In certain embodiments, multiple aliquots having the same assigned value are pooled or channeled together.

In one embodiment of the methods of the present invention, an active decision is required to rank or assign a value to an aliquot. In certain embodiments, a computer, controller, chip with integrated circuits, circuit board, electronic element, software, and/or algorithm is used to rank or assign a value to an aliquot.

3. Aliquot Channeling and Fluid Flow

In certain embodiments of the present invention, directing the flow or collection of an aliquot is based on the value assigned to the aliquot. For example, in an embodiment wherein a single type of rare particle is present in a fluid sample, an aliquot assigned a null or "0" value may be directed into a first channel (channeled) or waste outlet and an aliquot assigned a positive or "1" value may be directed into a second channel or collection chamber.

In other embodiments of the present invention, wherein more than one type of rare particle is present in the fluid sample, an aliquot may be channeled based on the particular composition of rare particles present in the aliquot. In one embodiment, an aliquot containing no rare particles may be directed into a first channel or waste outlet, an aliquot containing a first type of rare particle may be directed into a second channel or a first collection chamber, and an aliquot containing a second type or rare particle may be directed into a third channel or second collection chamber.

In certain embodiments, an aliquot containing more than one type of rare particle may be directed into a particular flow channel or collection chamber. Alternatively, the aliquot may be directed into a mixing or dilution chamber and subsequently the mixed or diluted aliquot may be further partitioned into sub-aliquots such that the rare cells are partitioned into different sub-aliquots. The rare cells in the sub-aliquots may then be detected again such that the rare cells can be separated from each other.

In one embodiment of the methods provided herein, the step of channeling (i.e., directing the flow or collection of the aliquots may be performed by the use of external fields or by creating flow disturbances.

In one aspect of the invention, once an aliquot is ranked, external fields may be used to alter the aliquot direction. The fields may include electric field, magnetic field, electrokinetic, electrophoretic, dielectrophoretic, hydrodynamic, gravitational, pneumatic or optical forces. Alternatively external flow disturbances may be induced with an introduction of materials immiscible with cell suspension, such as air, immiscible organic liquid, or microbeads.

In certain embodiments, the flow can be delivered by, for example, methods and devices that induce hydrodynamic fluidic pressure, which includes but is not limited to those that operate on the basis of mechanical principles (e.g. external syringe pumps, pneumatic membrane pumps, vibrating membrane pumps, vacuum devices, centrifugal forces, and capillary action); electrical or magnetic principles (e.g. electroosmotic flow, electrokinetic pumps piezoelectric/ultrasonic pumps, ferrofluidic plugs, electrohydrodynamic pumps, and magnetohydrodynamic pumps); thermodynamic principles (e.g. gas bubble generation/phase-change-induced volume expansion); surface-wetting principles (e.g. electrowetting, chemically, thermally, and radioactively induced surface-tension gradient); and the like.

In yet other embodiments, the fluid can be delivered or channeled by a fluid drive force provided by gravity feed, surface tension (like capillary action), electrostatic forces (electrokinetic flow), centrifugal flow (substrate disposed on a compact disc and rotated), magnetic forces (oscillating ions causes flow), magnetohydrodynamic forces and a vacuum or pressure differential.

In certain embodiments, Fluid flow control devices, such as those enumerated with regard to methods and devices for inducing hydrodynamic fluid pressure or fluid drive force, can be coupled to an input port or an output port of the present subject matter. In one example, multiple ports are provided at either or both of the inlet and outlet and one or more ports are coupled to a fluid flow control device.

B. Diagnostic and Prognostic Methods

In one aspect, the present invention provides a method for providing a subject a diagnosis or prognosis for a condition associated with the presence of a rare particle in a fluid sample, for example a biological fluid such as a blood sample.

In one embodiment the method comprises the steps of: (a) detecting the presence or absence of the rare particle in an aliquot of the biological fluid; (b) assigning a value to the aliquot based on the presence or absence of the rare particle; and (c) directing the flow or collection of the aliquot based on the assigned value.

In another embodiment, the method comprises the steps of: (a) contacting a biological fluid from the subject with a detection reagent under conditions suitable to transform the detection reagent into a complex comprising said detection reagent and a rare particle; (b) detecting the presence or absence of a complex formed in step (a) in an aliquot of the biological fluid; (c) assigning a value to the aliquot based on the presence or absence of a complex formed in step (a); and (d) providing a diagnosis or prognosis to the subject based on the assigned value.

In another embodiment, the step of detecting the presence of the rare particle comprises the sub-steps of: (i) interrogating the aliquot with an external source of electromagnetic radiation; and (ii) detecting fluorescence of the rare particle.

For more than 100 years, physicians have known that cancers spread by shedding cells into the blood. As blood carries these cancer cells from organ to organ, cancer metastasizes. These loose tumor cells are called Circulating Tumor Cells (CTC). In one aspect, the present invention offers accurate methods for counting and isolating these cancer cells from the peripheral blood.

Accurate detection of CTCs in blood turns out to be exceedingly difficult because of the astronomical number of red and white blood cells also present. With as many as 5 billion red blood cells and 5 million white blood cells co-existing to mask a single CTC, the problem of detecting CTCs is literally finding a needle in a haystack.

By accurately counting the number of cancer cells in blood, the present invention offers a real-time snapshot of the cancer spreading process. The most remarkable differentiation of a CTC blood test from the traditional prognostic tools (e.g., status of lymph nodes, tumor size, and morphologic features) is that the CTC blood test can be used to provide early feedback on whether a cancer treatment is effective. Patients undergoing the 6-month chemotherapy may have their CTC counts measured every 3-4 weeks; if the count remains high, the oncologist may deem the current treatment ineffective and prescribe new drugs. From the patients' perspective, having a CTC test can (1) provide a substantial savings by eliminating ineffective chemotherapy, which can cost between about $3,000-$10,000/month per drug, (2) grant them precious opportunities to find an effective treatment before it is too late. These reasons alone are important enough for oncologists to routinely prescribe expensive radiological imaging scans (e.g., CT or MRI). However, in one aspect, the present invention provides a rapid, inexpensive CTC test that is cheaper, safer, more reproducible, and provides the same, if not more accurate, prognostic information six weeks earlier than a radiological imaging scan. There is currently no biomarker test available that offers similar advantages.

Due to a high sensitivity in cancer cells detected, the methods described herein provide the potential of detecting cancer cells before their concentration reach the lower detection limit of competing technologies. This means that the methods provided herein are able to yield meaningful results earlier than competing technologies. Consequently, instead of limiting the use of the present technology to Stage IV metastatic cancer, oncologists may expand its use toward early diagnostic (i.e., Stage III, Stage II, Stage I, or metastatic, or pre-cancerous), for example by periodically prescribing the use of the methods provided herein to the general public not yet exhibiting symptoms of cancer. Generally healthy people do not have any CTCs in blood; if any CTC is detected in the unsuspecting patients using the present invention, then further tests, (e.g., CT, MRI,) can be prescribed to locate the tumors and confirm the status.

In another embodiment, tumor cells isolated using the present invention may be further subjected to subpopulation analysis (e.g., according to genotype or phenotype) to develop a targeted treatment. As an example, the isolated tumor cells can be incubated with fluorescent antibodies binding to specific drug targets to determine the presence or degree of expression of a drug target. Once the expression of the drug target is confirmed, an oncologist can be assured to choose from drugs specifically developed to target the expression. In one example, the isolated tumor cells may be incubated with fluorescent antibodies binding specifically to Her2 receptor to determine whether the breast tumor shedding CTCs is Her2-positive. If the isolated tumor cells exhibit high Her2 expression, oncologist may prescribe Herceptin (trastuzumab), since this drug is designed to target and block the function of HER2 protein overexpression. Other known drug targets, including BCR-ABL or PDGFR (targeted by drug Gleevec), ERBB2 (targeted by Herceptin), EFGR (targeted by Iressa, Tarceva), RAR-alpha (targeted by ATRA), Oestrogen receptor (targeted by Tamoxifen), aromatase (targeted by Letrazole), androgen receptor (targeted by Flutamide, Biclutamide), CD20 (targeted by Rituximab), VEGF-receptor (targeted by Avastin) can also be similarly screened from the isolated tumor cells before prescribing the appropriate chemotherapy regimen.

In a specific embodiment, the rare particle is a cancer cell or circulating tumor cell (CTC). In other embodiments, the rare cell may be a parasitic cell or organism, for example, a species of *Giardia* or *Cryptosporidium*, a erythrocyte infected with a species of *Plasmodium*, a lymphocyte or leucocyte infected with HIV, a fetal cell in maternal blood, a stem cell, a prion-infected cell, a CD4+ T-cell, and the like.

In one embodiment, a method for diagnosing malaria is provided, the method comprising detecting an erythrocyte infected with *Plasmodium* using an eDAR method and/or apparatus provided herein.

In another embodiment, a method for diagnosing an HIV infection is provided, the method comprising detecting a lymphocyte or leucocyte infected with the HIV virus using an eDAR method and/or apparatus provided herein.

In yet another embodiment, a method for diagnosing a disease associated with a prion is provided, the method comprising detecting a prior in a biological fluid from a human or other animal (e.g., a cow) using an eDAR method and/or apparatus provided herein. In one embodiment, the disease associated with a prion is mad cow disease.

1. Diagnosing Cancer

In one particular embodiment, the method comprises detecting a circulating tumor cell in a blood sample from a subject using an eDAR method and/or apparatus provided herein. In certain embodiments, the subject may be a patient who has previously been diagnosed with Stage I, Stage II, Stage III, or Stage IV cancer. In certain embodiments, wherein a CTC is detected in a blood sample from a patient previously diagnosed with cancer, the patient may be further diagnosed with metastatic cancer.

In one embodiment, a method is provided for diagnosing metastatic cancer in a subject that has previously been diagnosed with a solid tumor, the method comprising the steps of: (a) detecting the presence or absence of a CTC in an aliquot of a blood sample from the subject; (b) assigning a value to the aliquot based on the presence or absence of the CTC; and (c) directing the flow or collection of the aliquot based on the assigned value. In one embodiment, the absence of CTCs in the blood sample is correlated with the subject not having metastatic cancer. In another embodiment, the presence of at least one CTC in the blood sample is correlated with the subject having metastatic cancer. In yet another embodiment, the presence of at least a reference number of CTCs in the blood is correlated with the subject having metastatic cancer. In some embodiments, the method may further comprise a step of (d) diagnosing the subject as not having metastatic cancer if no CTCs are detected in the blood sample or diagnosing the subject as having metastatic cancer if at least one CTC is detected in the blood sample.

In a related embodiment, a method for monitoring a subject diagnosed with cancer is provided comprising detecting the presence or absence of a CTC in an aliquot of a blood sample from the subject using an eDAR method provided herein. In certain embodiments, the patient may be monitored for the progression of cancer to metastatic cancer at regular intervals, for example, at least once a year, at least twice a year, or at least about 3, 4, 5, 6, 7, 8, 9, 10, or more times a year. In some embodiments, the subject may be monitored about once a month, or at least about 2, 3, 4, 5, 6, 7, 8, 9, 10, or more times a month. In one embodiment, the absence of CTCs in the blood sample is correlated with the subject not having metastatic cancer. In another embodiment, the presence of at least one CTC in the blood sample is correlated with the subject having metastatic cancer. In yet another embodiment, the presence of at least a reference number of CTCs in the blood is correlated with the subject having metastatic cancer. In some embodiments, the method may further comprise a step of (d) diagnosing the subject as not having metastatic cancer if no CTCs are detected in the blood sample or diagnosing the subject as having metastatic cancer if at least one CTC is detected in the blood sample.

In embodiments wherein a CTC is detected in a blood sample, the method may further comprise a step of subjecting one or more aliquots identified as containing a CTC to further analysis to identify one or more characteristics of the CTC cell or cells. For example, an aliquot or pool of aliquots containing a CTC may be contacted with one or more detection reagents specific for one or more cancer-specific surface antigens. By determining which cancer-specific antigens are present on the surface of the CTCs, therapy can then be designed to target the expressed surface antigen. Non-limiting examples of cancer-specific surface antigens that can be assayed for include, without limitation, BCR-ABL or PDGFR (targeted by drug Gleevec), ERBB2 (targeted by Herceptin), EFGR (targeted by Iressa, Tarceva), RAR-alpha (targeted by ATRA), Oestrogen receptor (targeted by Tamoxifen), aromatase (targeted by Letrazole), androgen receptor (targeted by Flutamide, Biclutamide), CD20 (targeted by Rituximab), VEGF-receptor (targeted by Avastin), and the like. Accordingly, in certain embodiments, the method may further comprise a step of assigning a targeted therapy to the subject based on the detection of a specific surface antigen present on the CTC.

In certain embodiments, the further analysis can be performed using an eDAR method provided herein, for example by contacting the pooled aliquots with a plurality of differentially labeled detection reagents under conditions suitable to transform the detection reagents into complexes with the cancer-specific antigens present on the surface of the CTCs and detecting the complexes using a plurality of detection devices.

In other embodiments, the further analysis can be performed by coupling the initial eDAR method with a traditional flow cytometry or immunochemical method (e.g., immunoblot, ELISA, xMAP multiplex assay, etc.). In certain embodiments, the eDAR device used to detect the CTC may be in fluid communication with a second device or means for performing the further analysis.

In embodiments wherein a subject is diagnosed with metastatic cancer, the method may further comprise a step of assigning therapy for metastatic cancer to the subject.

In another particular embodiment, a method is provided for diagnosing a subject with cancer, the method comprising detecting a CTC in a blood sample taken from the subject. For example, detecting a CTC in a blood sample from a subject that has not been previously diagnosed with cancer. In some embodiments, the subject may have an increased risk of having or developing cancer, for example, the subject may have a family history of cancer, be a smoker, or otherwise been exposed to a carcinogenic substance (i.e., asbestos, benzene, cadmium, radon, radioactivity, and the like).

As such, in certain embodiments, a method is provided for monitoring a subject that has not been previously diagnosed with cancer, the method comprising the steps of: (a) detecting the presence or absence of a CTC in an aliquot of a blood sample from the subject; (b) assigning a value to the aliquot based on the presence or absence of the CTC; and (c) directing the flow or collection of the aliquot based on the assigned value. In one embodiment, the absence of CTCs in the blood sample is correlated with the subject not having metastatic cancer. In another embodiment, the presence of at least one CTC in the blood sample is correlated with the subject having cancer. In yet another embodiment, the presence of at least a reference number of CTCs in the blood is correlated with the subject having cancer or metastatic cancer. In some embodiments, the method may further comprise a step of (d) diagnosing the subject as not having cancer if no CTCs are detected in the blood sample or diagnosing the subject as having cancer if at least one CTC is detected in the blood sample.

In certain embodiments, the step of detecting the presence or absence of the CTC can be performed as described above, for example, by (i) contacting a biological fluid from the subject with a detection reagent under conditions suitable to transform the detection reagent into a complex comprising said detection reagent and a rare particle; and (ii) detecting the presence or absence of a complex formed in step (i) in an aliquot of the biological fluid, or by (i) interrogating the aliquot with an external source of electromagnetic radiation; and (ii) detecting fluorescence of the rare particle.

2. Methods for Providing a Prognosis

In one aspect, the present invention provides methods for providing a prognosis for a disease or condition associated with the presence of a rare particle in a biological fluid. In one embodiment, the method comprises the steps of: (a) detecting the presence or absence of the rare particle in an aliquot of a biological sample from a subject; (b) assigning a value to the aliquot based on the presence or absence of the rare particle; (c) directing the flow or collection of the aliquot based on the assigned value; and (d) providing either a good prognosis if no rare particles are detected in the sample or a poor prognosis if a rare particle is detected in the sample.

In other embodiments, the aliquot is assigned a value based on the quantity or the identity of the rare particle in the aliquot. In certain of these embodiments, a good or poor prognosis is provided based on the quantity of the rare particles in the sample. For example, in one embodiment, a good prognosis is provided if the quantity of the rare particles in the sample is less than a predetermined reference value and a poor prognosis is provided if the quantity of the rare particles in the sample is equal to or greater than the reference value.

In certain embodiments, a predetermined reference value may be associated with a likelihood of responding to a particular therapy or a likelihood of overall or disease free survival for a period of time, for example at least 6 month, or at least 1, 2, 3, 4, 5, 6, 7, 8, 9, 10, 15, 20, or more years.

In certain embodiments, the step of detecting the presence or absence of the rare particle can be performed as described above, for example, by (i) contacting a biological fluid from the subject with a detection reagent under conditions suitable to transform the detection reagent into a complex comprising said detection reagent and a rare particle; and (ii) detecting the presence or absence of a complex formed in step (i) in an aliquot of the biological fluid, or by (i) interrogating the aliquot with an external source of electromagnetic radiation; and (ii) detecting fluorescence of the rare particle.

In certain embodiments, a method provided herein may be used to provide a prognosis for any disease associated with a rare particle. In one embodiment, a method for providing a prognosis for malaria is provided, the method comprising determining the number of erythrocytes infected with *Plasmodium* in a blood sample from an individual using an eDAR method and/or apparatus provided herein and providing either a good prognosis if the total number of infected erythrocytes detected in the blood sample is less than a predetermined reference value or a poor prognosis if the total number of infected erythrocytes detected in the sample is equal to or greater than the reference value.

In another embodiment, a method for providing a prognosis for an HIV infection is provided, the method comprising determining the number of lymphocytes or leucocytes infected with an HIV virus in a blood sample from an individual using an eDAR method and/or apparatus provided herein and providing either a good prognosis if the total number of infected cells detected in the blood sample is less than a predetermined reference value or a poor prognosis if the total number of infected cells detected in the sample is equal to or greater than the reference value.

In yet another embodiment, a method for providing a prognosis for a disease associated with a prion is provided, the method comprising determining the number of prions in a biological fluid sample from a subject using an eDAR method and/or apparatus provided herein and providing either a good prognosis if the total number of prions detected in the sample is less than a predetermined reference value or a poor prognosis if the total number of prions detected in the sample is equal to or greater than the reference value.

In certain embodiments, a predetermined reference value may be associated with a likelihood of responding to a particular therapy or a likelihood of overall or disease free survival for a period of time, for example at least 6 month, or at least 1, 2, 3, 4, 5, 6, 7, 8, 9, 10, 15, 20, or more years.

In a specific embodiment, the present invention provides a method for providing a prognosis for a subject diagnosed with a solid tumor is provided. In one embodiment, the method comprises the steps of (a) detecting the presence or absence of a CTC in an aliquot of a blood sample from the subject; (b) assigning a value to the aliquot based on the presence or absence of the CTC; (c) directing the flow or collection of the aliquot based on the assigned value; and (d) providing either a good prognosis if no CTCs are detected or a poor prognosis if a CTC is detected.

In another embodiment, a method is provided for providing a prognosis for a subject diagnosed with metastatic cancer, the method comprising the steps of (a) detecting the presence or absence of a CTC in an aliquot of a blood sample from the subject; (b) assigning a value to the aliquot based on the number CTCs detected in the aliquot; (c) directing the flow or collection of the aliquot based on the assigned value; and (d) providing either a good prognosis if the total number of CTCs detected in the blood sample is less than a predetermined reference value or a poor prognosis if the total number of CTCs detected in the sample is equal to or greater than the reference value.

In certain embodiments, a predetermined reference value may be associated with a likelihood of responding to a particular therapy or a likelihood of overall or disease free survival for a period of time, for example at least 6 month, or at least 1, 2, 3, 4, 5, 6, 7, 8, 9, 10, 15, 20, or more years.

3. Monitoring Disease Progression or Response to Therapy

In another aspect, the present invention provides methods for monitoring the progression of a disease or the response to a therapy, the method comprising detecting a rare particle in a fluid sample using an eDAR method and/or apparatus provided herein.

In one embodiment, the method comprises the steps of: (a) detecting the presence or absence of the rare particle in a plurality of aliquots of a first biological sample taken from a subject at a first time; (b) assigning a value to the aliquots based on the presence, absence, quantity, or identity of the rare particle; (c) determining the total value of all the aliquots from the first sample; (d) detecting the presence or absence of the rare particle in a plurality of aliquots of a second biological sample taken from the subject at a second time; (e) assigning a value to the aliquots based on the presence, absence, quantity, or identity of the rare particle; (f) determining the total value of all the aliquots from the second sample; and (g) comparing the total value assigned to the first sample to the total value assigned to the second sample, wherein an increased value assigned to the second sample as compared to the first sample is correlated with a progression of the disease and/or a poor response to the therapy and/or a decreased value assigned to the second sample as compared to the first sample is correlated with a regression of the disease and/or a good response to the therapy.

In certain embodiments, the aliquots may further be directed into a particular channel or chamber (channeled) based on the value assigned for collection, further enrichment, or further analysis.

In certain embodiments, methods of monitoring disease progression or response to therapy may be employed on a regular basis after diagnosis of the disease or initiation of the treatment regime. For example, samples may be collected from a subject at least once a year, at least twice a year, or at least about 3, 4, 5, 6, 7, 8, 9, 10, or more times a year. In some embodiments, the subject may be monitored about once a month, or at least about 2, 3, 4, 5, 6, 7, 8, 9, 10, or more times a month.

In certain embodiments, wherein a progression of the disease or poor response to a therapy is found, the method may further comprise a step of assigning a therapy, increasing a dosage regime, changing a therapeutic regime, and the like.

In certain embodiments, the disease or condition associated with a rare particle may be cancer, malaria, HIV/Aids, a prion-related disease, or the like.

C. Methods of Monitoring Water Quality

In another aspect, the present invention provides a method for monitoring water quality by detecting one or more rare particle contaminant in a sample of water using an eDAR method or apparatus provided herein.

In one embodiment, the method comprises the steps of (a) detecting the presence or absence of a water contaminant in an aliquot of a sample taken from a water source; (b) assigning a value to the aliquot based on the presence, absence, quantity, or identity of the water contaminant in the aliquot; and (c) directing the flow or collection of the aliquot based on the assigned value, whereby the quality of the water source is determined based on the total value assigned to all of the aliquots detected in the method.

In certain embodiments, the water source may be a lake, pool, river, stream, or other natural body of water. In certain of these embodiments, the water may be tested to determine or predict the impact a man made object or activity has or will have on the body of water or to assess the feasibility or safety of using the body of water to supply drinking water to a population.

In other embodiments, the water source may be a pool or pond at a water treatment plant, a reservoir, a water tower, or other body of water collected for the purpose of supplying drinking water to a population. In certain of these embodiments, the water may be tested to assess the feasibility or safety of using the body of water to supply drinking water to a population.

In certain embodiments a method provided herein may be used to regularly monitor the quality of a water source used to supply drinking water to a population, for example at a water treatment plant or in a water tower or reservoir. In such an embodiment, the water source may be monitored at least once a year, at least twice a year, or at least about 3, 4, 5, 6, 7, 8, 9, 10, or more times a year. In some embodiments, the subject may be monitored about once a month, or at least about 2, 3, 4, 5, or more times a month. In yet other embodiments, the water may be tested at least once a week, or at least 2, 3, 4, 5, 6, or more times a week, or at least daily or at least 2, 3, 4, 5, 6, 7, 8, 9, 10, or more times a day.

In other embodiment, a method provided herein may be used to determine the feasibility or safety of using a body of water to supply drinking water to a population after a natural disaster (e.g., after a hurricane, tsunami, or earthquake), accident, or act of terrorism.

Methods of testing or monitoring water safety or quality may comprise the detection of a rare particle that is a water contaminant, for example a parasite such as a species of *Giardia, Cryptosporidium*, or other organic or inorganic water contaminant that when present at low quantities poses a public health risk.

D. Apparatuses

In one aspect, the present invention provides a device for detecting a rare particle in a biological fluid.

In one embodiment, the device comprises: (a) at least a first input channel; (b) at least two exit channels; (c) at least one detector capable of detecting one or more rare particles in an aliquot of the biological fluid; (d) a mechanism for directing the flow of the aliquot; and (e) a ranking device capable of assigning a value to the aliquot based on the presence, absence, identity, composition, or quantity of the rare particles in the aliquot, wherein the computer is in communication with the detector and the mechanism for directing the flow of the aliquot.

In some embodiments, the apparatus further comprises a source for interrogating the aliquot. In other embodiments, wherein the rare particle or cell intrinsically exhibits chemiluminescence or bioluminescence, the apparatus may not require a source for interrogating the aliquot.

In certain embodiments, the apparatus provided herein may comprise a flow channel enclosed by walls and/or microfabricated on a substrate, with design features to minimize inadvertent damage to rare cells. Reducing inadvertent damage of rare cells reduces the rate of false-negative which could lead to erroneous patient diagnosis or prognosis. The flow channel may further comprise channels with hydrodynamically designed apertures to exclude biological cells with minimal stress or damage as described in US Patent Application Nos. 2007/0037172 and 2008/0248499. Such channels, referred to in the aforementioned patent applications as channels with one-dimensional ("1-D") apertures, reduce the hydrodynamic pressure experienced by the cells during the cell exclusion process and therefore reduce the likelihood of cell lysis. Channels with 1-D apertures may be strategically arranged in an array according to "effusive filtration" configuration as described in U.S. Pat. No. 2008/0318324 to further re-direct, partition, dampen, or disperse the flow, consequently reducing the force of impact experienced by the cells at the moment of exclusion. The walls that enclose the flow channel may be fabricated using a UV-curing process in accordance with the procedures described in PCTPCT/US2009/02426, from a biocompatible substrate material that is a medical-device grade polymer, so that the eDAR apparatus would be in compliance with regulations governing medical device manufacturing.

1. Mechanisms for Directing the Flow of an Aliquot

In certain embodiments, the mechanism for directing the flow directs the flow of the aliquot into either a first exit channel if the aliquot contains a rare particle or a second exit channel if the aliquot does not contain a rare particle.

In another embodiment, the mechanism for directing the flow directs the flow of an aliquot containing a rare particle into one of a plurality of exit channels depending on the identity, composition, or quantity of the rare particle.

In certain embodiments, the mechanism for directing the flow of the aliquot comprises an electrode, a magnetic element, an acoustic element, an electro-actuated element, an electric field, or a magnetic field.

In yet other embodiments, the mechanism for directing the flow of the aliquot comprises one or more electro-actuated valves or pistons, wherein the valves or pistons control the flow of a liquid in at least a first directional flow channel that intersects with the first input channel and the two exit channels at a first junction.

In one embodiment, solenoid pistons are subcomponents of electro-actuated solenoid valves. In another embodiment, solenoid pistons are embedded in device by molding. In yet another embodiment, the embedded solenoid pistons may be replaced by solenoid valves in fluidic communication via tubings.

In one particular embodiment, an apparatus provided herein may comprise one or more electrodes for tracking and/or manipulating the trajectory or flow of a particle, aliquot, or fluid sample. In certain embodiments, the electrode may enhance the separation of an aliquot based on phenomena such dielectrophoresis or electrowetting.

In certain embodiments, the apparatuses of the present invention may comprise one or more acoustical elements for tracking and/or manipulating the trajectory or flow of a particle, aliquot, or fluid sample. In certain embodiments, acoustical elements may be used to manipulate the trajectory of select particles or cells with acoustical energy (e.g., acoustophoresis, ultrasonic or megasonic waves) to improve cell separation based on the response of cells to compressive pressure waves.

In another embodiment, the apparatuses provided herein may further comprise a magnetic element for the separation of a rare particle or cell bound to or bound by a magnetic particle. In certain embodiments, the magnetic element may enhance the separation of an aliquot, particle, or cell based on the magnetic susceptibility of the cells or the micro-magnetic or nano-magnetic particles attached to a particle or cell.

In certain embodiments, an apparatus provided herein may comprises the use of fluidic pressure changes, flow-rate changes, or electroosmostic flow changes to manipulate the trajectory of select particles or cells.

2. Detection Devices

In certain embodiments, the detector is selected from the group consisting of a camera, an electron multiplier, a charge-coupled device (CCD) image sensor, a photomultiplier tube (PMT), an avalanche photodiode (APD), a single-photon avalanche diode (SPAD), and a complementary metal oxide semiconductor (CMOS) image sensor.

In certain embodiments, an apparatus provided herein may comprise a photo, electro, acoustical or magnetic detector to track the motion of select cells or to enumerate select particles or cells present in an aliquot.

In some embodiments, an apparatus or method provided herein may incorporate fluorescence (single or multi-color) microscopy imaging in various configurations, which include but are not limited to bright-field, epi, confocal, DIC (differential interference contrast), dark-field, Hoffman, or phase-contrast.

In some embodiments, the apparatuses provided herein may comprise a plurality of detection devices, for example, at least 2, 3, 4, 5, 6, 7, 8, 9, 10, or more detection devices. Multiple detection devices may be necessary for performing a methods of the present invention, for example, wherein more than one rare particle or cell is present in a fluid sample, more than one cell marker is being used to differentiate different cell types, or multiple detection reagents are being detected simultaneously.

3. Interrogation Devices

In certain embodiments, the apparatuses provided herein may further comprise a source for interrogating or exciting a detectable moiety present in an aliquot. In certain embodiments, the source for interrogating is selected from, for example, a laser (solid state, diode-pumped, ion, or dye), a light-emitting diode (LED), a lamp, an arc discharge, a magnetic pulse, or a natural light source.

In some embodiments, the apparatuses provided herein may comprise a plurality of interrogation devices, for example, at least 2, 3, 4, 5, 6, 7, 8, 9, 10, or more detection devices. Multiple interrogation devices may be necessary for performing a methods of the present invention, for example, wherein more than one rare particle or cell is present in a fluid sample, more than one cell marker is being used to differentiate different cell types, or multiple detection reagents are being detected simultaneously.

4. Ranking Devices

In certain embodiments, a ranking device may be selected from a computer, a controller, a chip with integrated circuits, a circuit board, an electronic element, software, an algorithm, or a combination thereof.

5. Flow Channels and Chambers

In certain embodiments, an apparatus provided herein may comprise a plurality of flow channels, including one or more input flow channels (i.e., channels that bring an aliquot to a detection volume) and one or more output channels (i.e., channels that take an aliquot away from a detection volume). In some embodiments, an apparatus as provided herein may comprise a combination of at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or more input channels and at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or more output channels.

In certain embodiments, an apparatus may comprise multiple flow channels connecting to the main channel to inject additional fluid to alter the local velocity.

In one embodiment, an apparatus provided herein may comprise a flow channel or chamber enclosed by walls fabricated from materials including, but not limited to, polymeric materials (polydimethylsiloxane (PDMS), polyurethane-methacrylate (PUMA), polymethylmethacrylate (PMMA), polyethylene, polyester (PET), polytetrafluoroethylene (PTFE), polycarbonate, parylene, polyvinyl chloride, fluoroethylpropylene, lexan, polystyrene, cyclic olefin copolymers, polyurethane, polyestercarbonate, polypropylene, polybutylene, polyacrylate, polycaprolactone, polyketone, polyphthalamide, cellulose acetate, polyacrylonitrile, polysulfone, epoxy polymers, thermoplastics, fluoropolymer, and polyvinylidene fluoride, polyamide, polyimide), inorganic materials (glass, quartz, silicon, GaAs, silicon nitride), fused silica, ceramic, glass (organic), metals and/or other materials and combinations thereof.

In certain embodiments, a wall materials can be fabricated of porous membranes, woven or non-woven fibers (such as cloth or mesh) of wool, metal (e.g. stainless steel or Monel), glass, paper, or synthetic (e.g. nylon, polypropylene, polycarbonate, parylene, and various polyesters), sintered stainless steel and other metals, and porous inorganic materials such as alumina, silica or carbon.

In certain embodiments, the apparatuses provided herein may comprise a flow channel or chamber that has been pre-treated with a chemical or biological molecule. For example, a channel or chamber may be treated with an anticoagulant compound to prevent or reduce the association of a particle in the fluid sample, a compound that preferentially binds to a particle in the fluid sample, for example a rare particle or cell, or a compound that prevents or reduces the agglomeration or aggregation of a particle in the fluid sample.

In one embodiment, the channel or chamber surfaces may be treated with anticoagulant compounds, compounds that preferentially bind to circulating tumor cells, or compounds that prevent the sticking of cells.

In certain embodiments, a channel or chamber surface may be modified chemically to enhance wetting or to assist in the adsorption of select cells, particles, or molecules. Surface-modification chemicals may include but not limited to silanes such as trimethylchlorosilane (TMCS), hexamethyldisilazane (HMDS), (Tridecafluoro-1,1,2,2-tetrahydrooctyl)trichlorosilane, chlorodimethyloctylsilane, Octadecyltrichlorosilane (OTS) or γ-methacryloxypropyltrimethyoxy-silane; polymers such as acrylic acid, acrylamide, dimethylacrylamide (DMA), 2-hydroxyethyl acrylate, polyvinylalcohol (PVA), poly(vinylpyrrolidone (PVP), poly (ethylene imine) (PEI), Polyethylene glycol (PEG), epoxy poly(dimethylacrylamide) (EPDMA), or PEG-monomethoxyl acrylate; surfactants such as Pluronic surfactants, Poly(ethylene glycol)-based (PEG) surfactants, sodium dodecylsulfate (SDS) dodecyltrimethylammonium chloride (DTAC), cetyltriethylammonium bromide (CTAB), or Polybrene (PB); cellulose derivatives such as hydroxypropylcellulose (HPC), or hydroxypropylmethylcellulose (HPMC); amines such as ethylamine, diethylamine, triethylamine, or triethanolamine, fluorine-containing compounds such as those containing polytetrafluoroethylene (PTFE) or Teflon.

6. Means for Background Reduction

In certain embodiment, the apparatuses provided herein may further comprise a means for reducing excessive background signal and/or improving the signal-to-noise ratio. By reducing excessive background signal and increasing the signal-to-noise ratio, the sensitivity of detection is enhanced as the weak signals from even a highly diluted aliquot can be accurately detected. In other words, the better the signal-to-noise ratio, larger an aliquot can be scanned. As a direct result, the fluidic throughput is correspondingly increased since fewer (but larger) aliquots need to be scanned.

Figure 3:
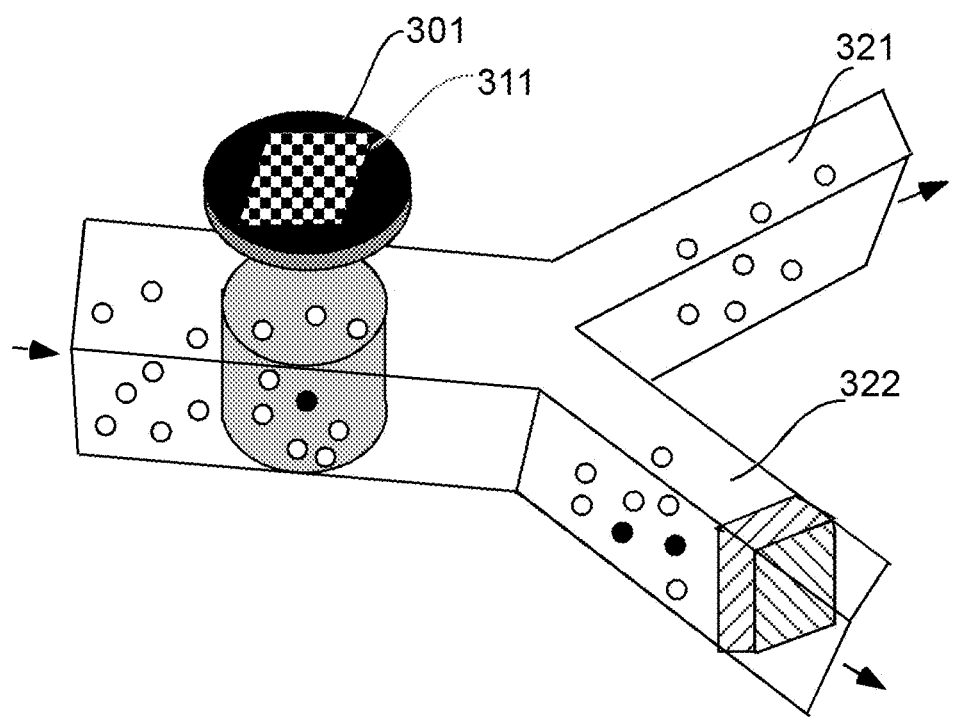
FIG. 3 illustrates a mask with closely spaced apertures to improve the signal-to-noise ratio as used in eDAR.

In one embodiment, the means for reducing background signal comprises a mask. A mask can consist of any number of apertures of any shape or size, positioned in any orientation with or without any periodic spacing. For example, FIG. 3 illustrates a mask (301) containing an array of apertures (311), positioned between the detection volume and a detector to selectively allow through a detectable characteristic.

In certain embodiments, a mask may comprise an optical element that selectively pass through certain wavelengths of light, for example, a low-pass, high-pass, or band-pass filter, or acousto-optic modulator, spatial-light modulator, light-chopper, fabricated hologram, physical aperture, or galvo scanner.

In other embodiments, a mask can consist of magnetic elements that selectively prevent passage of a magnetic field.

In some embodiments, other devices that accomplish similar gains in signal-to-noise ratio may be used in place of or in conjunction with a mask. For example, in certain embodiments a device selected from a lock-in amplifier, a scanning detector, a modulated interrogator or detector, or any apparatuses that modulate frequency or intensity may be used to increase the signal-to-noise ratio.

In yet other embodiments, detectors with spatial-modulation functionality of a mask directly incorporated within may be used in conjunction with the apparatuses provided herein. In certain embodiments, a separate mask is not present. In other embodiments, a separate mask is also present. Non-limiting examples of detectors with incorporated mask functionality include photodiode arrays or cameras with spatial pixelation such that signals of individual photodiodes or select pixels of cameras may be removed or kept.

7. Additional Elements

In certain embodiments, the apparatuses provided herein may further comprise additional elements useful for performing assays, processes, or tests in a fashion that is coupled to the eDAR methods provided herein.

In one embodiment, an apparatus provided herein may further comprise one or more resistive heating elements to perform on-chip cellular assays such as Polymerase Chain Reaction (PCR) or Real-Time Polymerase Chain Reaction (RT-PCR).

In yet other embodiments, an apparatus provided herein may further comprises one or more electrodes, for example, to conduct on-chip chemical assay such as electrophoresis or eletrochromatography.

In another embodiment, an apparatus provided herein may further comprise a filter element. In a particular embodiment, the filter element may be in the form of microposts, microimpactors, microsieves, channels with apertures smaller than bioparticles, channels with apertures such that a bioparticle is prevented from entering an apertured but fluid is allowed to continue to flow around the bioparticle through the aperture ("1-D channels"), microbeads, porous membranes, protrusions from the walls, adhesive coating, woven or non-woven fibers (such as cloth or mesh) of wool, metal (e.g. stainless steel or Monel), glass, paper, or synthetic (e.g. nylon, polypropylene, polycarbonate, parylene, and polyester), sintered stainless steel or other metals, or porous inorganic materials such as alumina, silica, or carbon.

For example, FIG. 16 illustrates a filter element (1622), which may be disposed in a channel, such as an outlet channel (1621), to selectively allow the passage of fluid portion while retaining the desired bioparticles.

In yet another embodiment, an apparatus provided herein may be coupled to a conventional flow cytometer.

For example, FIG. 16 illustrates an outlet channel (1621) that may be in fluidic communication to a conventional flow cytometer (with or without filter element 1622) such that discrete aliquot 1661 containing rare cell 1602 is further examined or sorted serially (one cell by one cell).

IV. Examples

A. Example 1

An Example of an eDAR Apparatus with a Single Inlet and Outlet Port for the Detection or Quantitation of Rare Particles in a Fluid.

Figure 4:
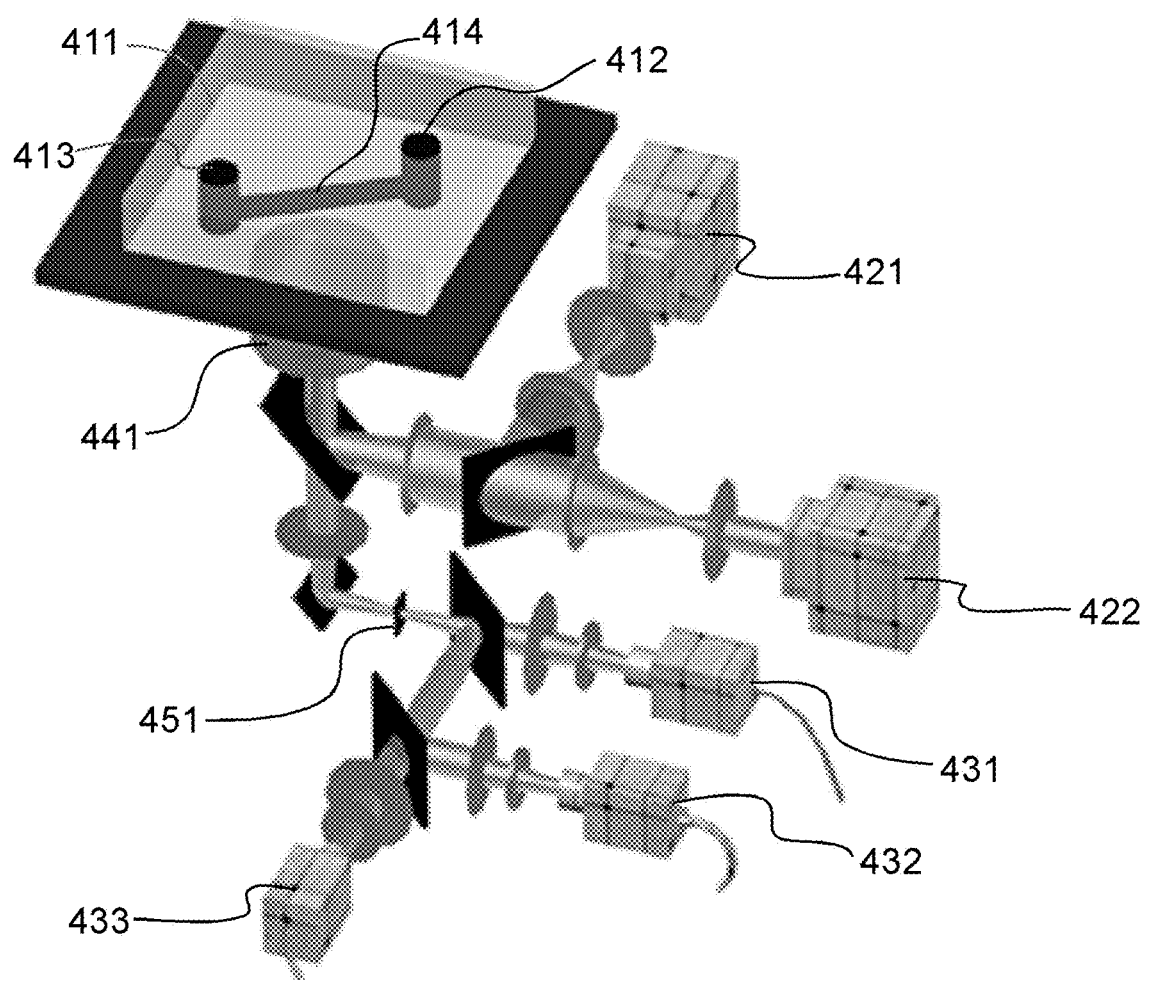
FIG. 4 illustrates an eDAR apparatus consisting of a single flow channel, 2 lasers, and three detectors.

FIG. 4 shows an example of eDAR apparatus consisting of a device (411) to aliquot a cell suspension, an interrogation device (421 and 422), a detection or imaging device (431, 432, and 433), and a ranking device (computer not shown). In this particular example, a device (411) to aliquot a cell suspension may consist of a fluidic channel (414) contained within walls and fluidic ports (412 and 413). A laser serves as an interrogation device. An inverted microscope with photodiodes, photomultipliers, or cameras is used as a detection device. A mask (451) is placed in a path between the channel (414) and the detection devices (431, 432, and 433). A computer accepts the signal from the detection device and through an algorithm ranks the aliquot. The computer then directs the aliquot into the proper channel based on the value of the ranking (i.e., the presence, absence, quantity, identity, or composition of rare particles in the fluid sample). Although FIG. 4 illustrates three detection devices (431, 432, and 433) and two interrogation devices (421 and 422), in practice eDAR may consist of only one detection device and one interrogation device, or multitudes of detection devices and interrogation devices.

In one use of the apparatus illustrated in FIG. 4, the interrogation devices (421 and 422) consisted of a 488 nm solid-state diode pumped laser and a 633 nm HeNe laser which are directed into an inverted microscope. The two laser beams were shaped using cylindrical optics to form a collimated elliptical beam with an aspect ratio of 10 to 1 prior to entering the microscope objective. Using a combination of half-waveplate and polarizing beam splitter, the intensity of each beam could be adjusted, while mirrors independently steered the light to create a spatially co-localized excitation region. The fluorescence from bioparticles was split into three wavelength bands by two dichroic mirrors before passing through the bandpass filters and refocused onto the three single-photon avalanche diodes (SPADs; 431, 432, and 433). One SPAD collected fluorescence in the wavelength range of 560-610 nm, a second SPAD collected fluorescence in the range of 645-700 nm, and a third SPAD collected in the range of 500-540 nm. The SPAD outputs were directed to a computer with a counter/timer board and analyzed with several algorithms.

B. Example 2 eDAR Apparatus with Two Outlet Ports for the Detection or Quantitation of Rare Particles in a Fluid.

Figure 5:
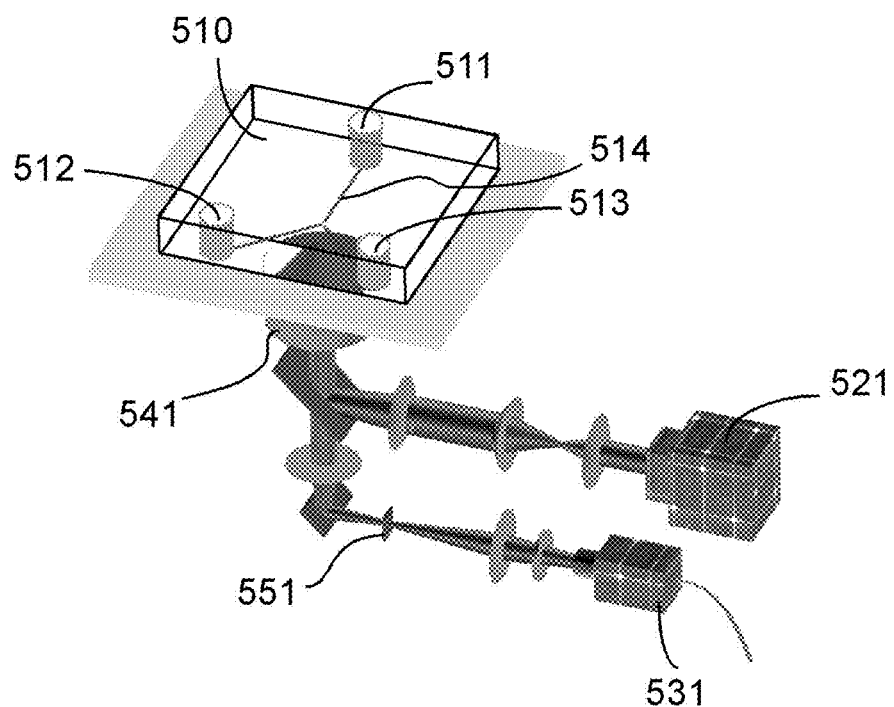
FIG. 5 illustrates an eDAR apparatus consisting of three flow channels, a laser, and a detector.

FIG. 5 illustrates an eDAR apparatus consisting of a device to aliquot cell suspension (510), an interrogation device (521), a detection or imaging device (531), a ranking device (computer not shown), and an apparatus to direct aliquot according to the assigned ranking. This apparatus also includes a single inlet port (511), two outlet ports (512 and 513), and three fluidic channels (514) joined at a single point to aliquot the fluid. A laser serves as the interrogation device (521) and an inverted microscope with photodiodes, photomultipliers, or cameras serves as detection device (531). A mask (551) is placed between the channels (514)

and the detection device (531). A computer accepts the signal from the detection device and ranks the aliquot through an algorithm. The device then utilizes an electrical, magnetic, hydrodynamic, or pneumatic mean to direct the aliquot into either outlet 512 or outlet 513 according to the assigned ranking.

Figure 6:
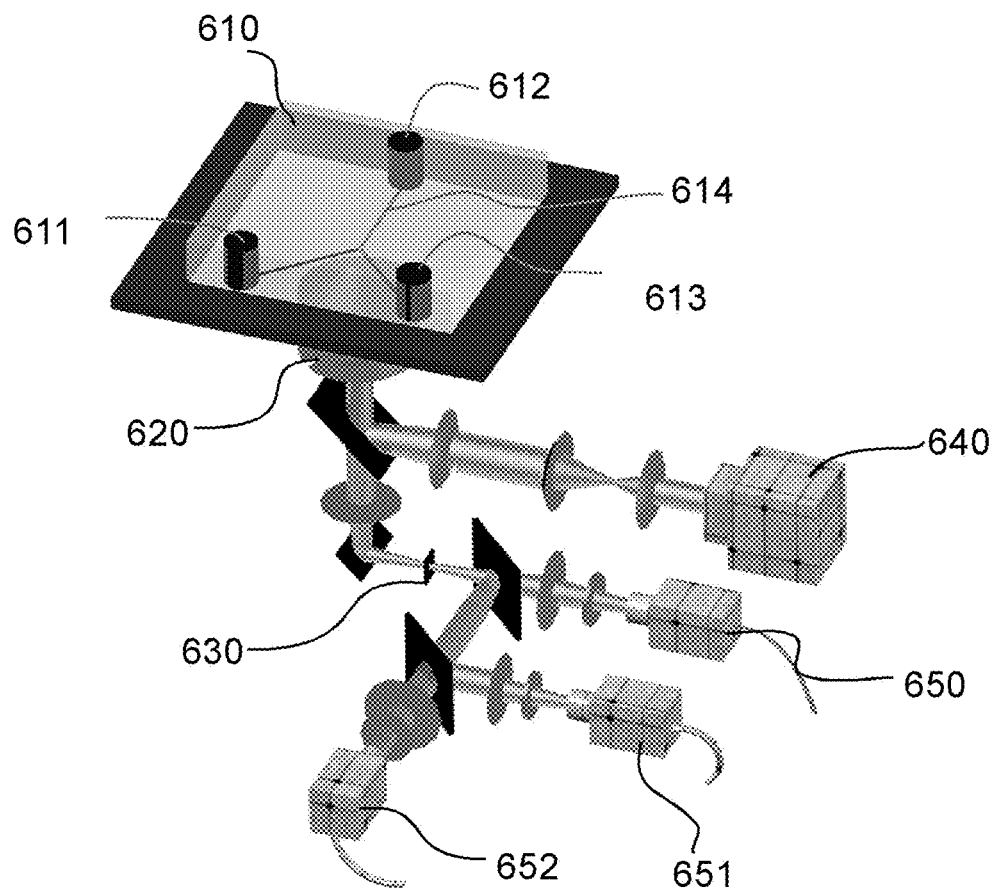
FIG. 6 illustrates an eDAR apparatus consisting of three flow channels, a laser, and three detectors.

In addition to the eDAR apparatus described above, which has a single interrogation device and a single detection devise, multiple interrogation and detection devices may be used in conjunction with the eDAR apparatuses described herein. For example, FIG. 6 illustrates an eDAR apparatus with one interrogation device (640) and three detection devices (650, 651, and 652).

C. Example 3 eDAR Apparatus with Multiple Inlet and/or Outlet Ports for the Detection or Quantitation of Rare Particles in a Fluid.

Figure 7:
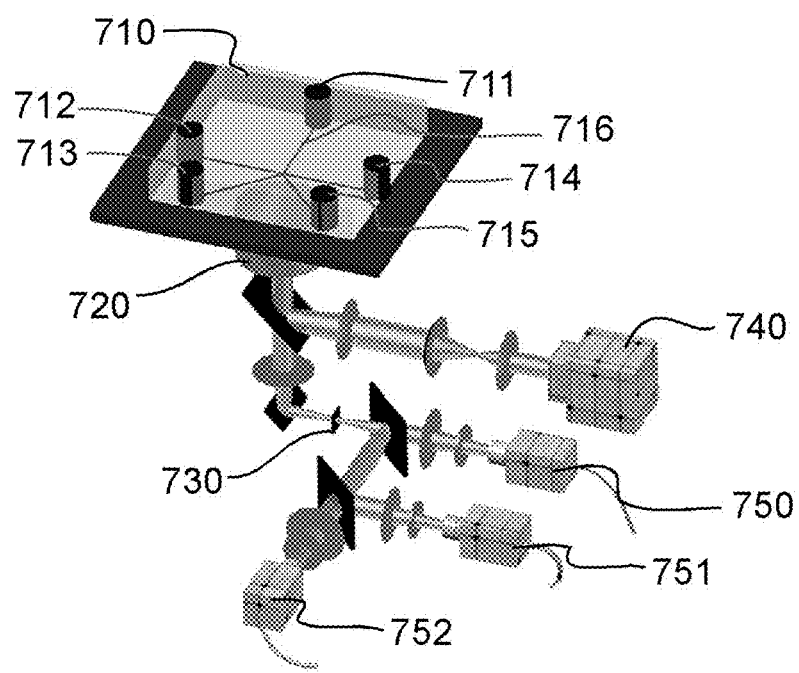
FIG. 7 illustrates an eDAR apparatus consisting of five flow channels, a laser, and three detectors.

In various aspects of the invention, an eDAR apparatus may consist of multiple inlet and/or outlet ports. For example, FIG. 7 illustrates a device (710) to aliquot suspension with five ports (711, 712, 713, 714, and 715) and five fluidic channels 716 joined at a single point. One or more ports may be used as fluidic inlet; one or more ports may be used as fluidic outlet. For example, the apparatus may be used such that two ports are used as inlet ports and three ports are used as outlet ports, or it may be used such that one port is an inlet port and four ports are outlet ports, etc. In theory, the device (710) may contain any number of fluidic inlets and outlets and any number of fluidic channels. These fluidic channels may be joined at more than one point and the joining point need not be circumscribed by the fluidic inlets or outlets.

D. Example 4

Detection of Circulating Tumor Cells (CTCs) in the Blood of Breast Cancer Patients by the Use of eDAR.

Freshly venipunctured blood from Stage IV metastatic breast cancer patients was drawn from a single puncture into three separate tubes. The first blood portion (first tube) was discarded to avoid possible contamination of epithelial cells from skin puncture. A second portion was collected into Veridex's CellSave tube containing stabilizing reagents for circulating tumor cell detection using a Veridex's CellSearch system. A third portion was collected into a collection tube containing EDTA anticoagulant for separate analysis using eDAR.

The third portion was incubated with enzymes, fixatives, permeability reagents, and fluorescent antibodies targeting pan-cytokeratin, CD45, and Epithelial Cell Adhesion Molecule (EpCAM). A positive identification of circulating tumor cell is defined as a cell expressing pan-cytokeratin and EpCAM, but not CD45. CD45 is commonly known as leucocyte common antigen and is indicative of a white blood cell. An object bound with all three antibodies is deemed false-positive, frequently a result of protein aggregation.

Briefly, the 5 to 10 mL antibody-labeled blood samples were flowed through an eDAR apparatus as described in Example 1 at a flow rate of between about 10-500 µL/min, using a compressed air source supplying 7.6 psi to drive the flow. The eDAR apparatus was operating in the continuous flow (simultaneous) mode. For these experiments, microchannels that were 200 µm wide by 50 µm tall were used. For interrogation of the labeled antibody complexes, line-confocal excitation beams were provided at both 488 nm and 633 nm, which illuminated a sheet of light that was about 5-10 µm thin. As such, the line-confocal detection volume had dimensions of about 200 µm (width)×50 µm (height)×10 µm (thickness), providing a detection volume of about 0.1 nL. Three SPAD detection devices were operating at 10,000 Hz sampling rate, configured to detect fluorescence signals emanating from the cells at 450-610 nm, 645-700 nm, and 500-540 nm. At this rate, each aliquot was on the order of 1 nL to 50 nL, estimated to contain 5-250 white blood cells and 5,000-25,000 red blood cells. For a sample of 5-10 mL, it thus takes between 10-20 min to process the sample at a flow rate of 500 µL/min. A 5 mL sample processed in this fashion will be divided into 10,000 aliquots having a volume of 50 nL each.

As such, if an eDAR apparatus having two outlet channels was used, a 5 mL sample containing 200 CTCs can be reduced to a volume of 10 µL in only 10 minutes, without the use of a filter. If the eDAR apparatus was further in liquid contact with a flow cytometer, All of the 200 CTC cells present in the 5 mL sample could be counted and/or individually isolated in only 2% of the normal time by implementing an eDAR step prior to the flow cytometry.

Figure 8:
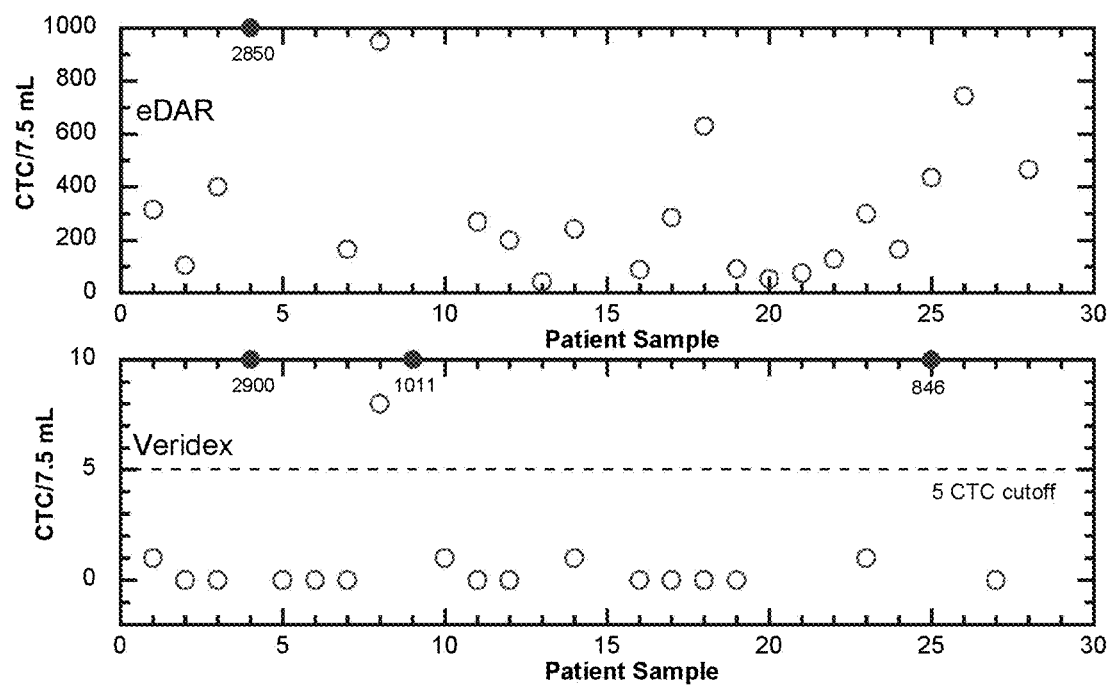
FIG. 8 shows a comparison in circulating tumor cell (CTC) counts from blood using eDAR (upper panel) and a commercial instrument (Veridex's CellSearch, lower panel).
Figure 10A:
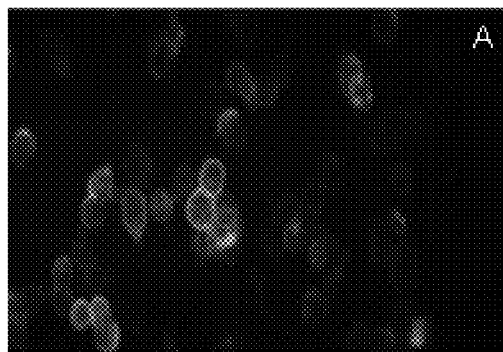
FIGS. 10A-10D show optical images of cancer stem cells distinguished from ordinary cancer cells. Arrowheads indicate cancer stem cells (CD44+/CD24−).
Figure 10B:
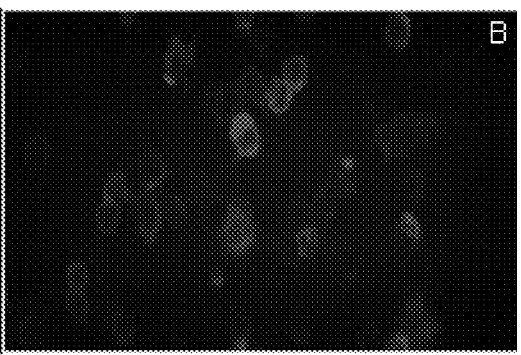
Figure 10C:
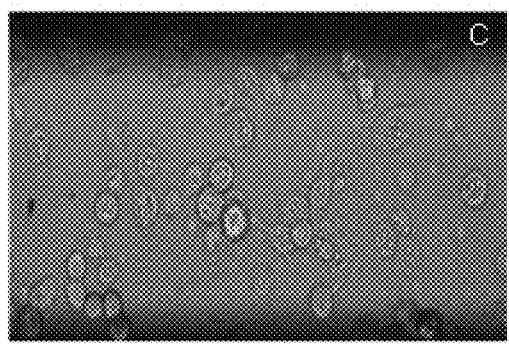
Figure 10D:
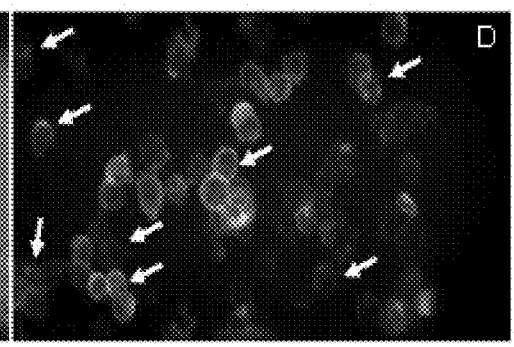

FIG. 8 shows CTC counts from 27 blood samples from Stage IV breast cancer patients (of multiple patients drawn on different dates) using Veridex's CellSearch system (lower panel) and eDAR (upper panel). As can be readily noted, most patient samples registered zero CTC counts using CellSearch system. In contrast, more than 50% of the same patient blood draws analyzed by eDAR were found to contain 200-400 CTC counts. This amply demonstrates a hundred times more sensitivity with the use of eDAR, as compared to the use of Veridex's commercial CellSearch system. The heightened sensitivity of eDAR is attributable to accurate discrimination between CTCs and background by aliquot ranking and the use of a mask.

As also shown in FIG. 8, 100% of the patient samples analyzed by eDAR indicated the presence of CTCs, whereas only 40% of the patient samples analyzed by Veridex's CellSearch system indicated any presence of any CTCs. This demonstrated a significantly lower rate of false-negative provided by eDAR. High rate of false-negative in a CTC test can lead to an inaccurate prognosis of metastasis and give patients a false sense of security that the existing treatment regimen is sufficient.

Exemplary images of a CTC detected by this eDAR method are provided in FIG. 9. Briefly, this figure shows the optical images of cancer cells trapped from patient blood using eDAR (arrows mark CTCs) under various illumination. FIG. 9A is a brightfield image of a CTC amidst red blood cells. FIG. 9B is a fluorescence image indicating the presence of pan-cytokeratin. FIG. 9C is a fluorescence image indicating the absence of CD45, hence ruling out the possibility of false-identifying a white blood cell as a CTC.

E. Example 5

Detection of Cancer Stem Cells Among a Population of Cancer Cells.

Cancer cells segregated by eDAR may be further analyzed to distinguish the subpopulations within the biological fluid. By perfusing with additional fluorescent antibodies targeting specific proteins, some cancer cells may be distinguished from others. For example, cancer cells that express CD44 but not CD24 proteins have recently been called cancer stem cells for their association with high metastatic potential. Other proteins may be associated with various traits of cells.

For example, FIG. 10 demonstrates the identification of breast cancer stem cells (marked with arrowheads). Briefly, breast cancer cells (MCF-7) were labeled with Alexa 488-anti-CD44 (positive) and Alexa 647-anti-CD24 (negative). FIG. 10A is a fluorescence image (500-540 nm) for detecting Alexa 488-anti-CD44 (green); FIG. 10B is a fluorescence image (645-700 nm) for detecting Alexa 647-anti-CD24 (red); FIG. 10C is the brightfield image. FIG. 10D is a composite image indicating CD44+/CD24− (arrows indicate cancer stem cells). Approximately 25% of cancer cells were found to express CD44 but not CD24 and thus meet the criteria for cancer stem cells. In this fashion, eDAR may be used to distinguish sub-populations of cancer cells in a biological fluid.

F. Example 6 eDAR Detection Using Discrete Aliquots.

In one example of the methods provided herein, eDAR may operated by using discrete aqueous aliquots that are separated by an immiscible phase to encapsulate bioparticles prior to the detection step. FIG. 16 illustrates an eDAR apparatus operating in this fashion. For example, a cell suspension containing undesired cells (1601) and desired rare cells 1602 is partitioned into discrete aliquots (1631, 1641, 1651, and 1661), which are separated from one another by an immiscible phase (1642). The discrete aliquots are directed to flow from left to right in a flow channel (1603). As aliquot 1641 traverses the detection volume (1604; cylindrical outline), multiple cells encapsulated within the discrete aliquot (1641) are detected simultaneously. If no desired cells are detected, the discrete aliquot (1641) is ranked as null and directed toward Channel 1611 (see, for example, aliquot 1651). If any desired rare cells are detected, the discrete aliquot is ranked as nonzero and is directed toward Channel 1621 (see, for example, aliquot 1661).

In one embodiment, filter element 1622 may be disposed in channel 1621 to selectively allow the passage of fluid portion while retaining the desired bioparticles. In one embodiment, and eDAR apparatus may be coupled to a conventional flow cytometer. For example, in FIG. 16, channel 1621 may be in fluidic communication to a conventional flow cytometer (with or without filter element 1622), such that discrete aliquot 1661 containing rare cell 1602 is further examined or sorted serially (one cell at a time).

The immiscible phase (1642) may be continuous (i.e., surrounds the discrete aliquots entirely) as illustrated in FIG. 16 or segmented (i.e., immiscible phase 1642 occupies only the spacing between discrete aliquots but does not completely surround the aliquots).

G. Example 7

As an example of the utility of one aspect of the present invention, if a 10-mL cell suspension contains only 9 desired rare cells amidst 10 billion undesired cells, eDAR, in the simplest form, would require the detection of a characteristic from the desired cells contained in 10 aliquots. Since there are only 9 desired cells, at least one aliquot would be devoid of the desired cells and can be ranked as null and discarded immediately. The undesired cells contained in the discarded portion would not need to be screened individually. Consequently, with merely 10 aliquots at least 1/10 of total volumes is immediately discarded and 1/10 of the undesired cells (contained within the discarded volume) would not need to be detected individually. To put it in perspective, that is 1 billion undesired cells eliminated as an ensemble with one decision. With current state-of-the-art cell sorter operating at the extreme speed of 70,000 objects/sec, this one decision resulted in 1,000,000,000/70,000=14,300 sec or 4 hours of time saved. This results in a significant increase in time efficiency.

Following from the scenario presented above, suppose if the 10-mL cell suspension is partitioned into 100 aliquots of 100 µL each, since the entire volume of cell suspension contains only 9 desired cells, at least 91 portions would not contain any desired cells. Therefore by performing only 100 scans and make 100 decisions, 91 aliquot×100 µL=9.1 mL can be immediately eliminated. The cells contained within the discarded portions would be 9.1 billion cells, or 91% of the undesired cells are eliminated within 100 decisions.

H. Example 8

FIG. 1 illustrates a particular embodiment of the invention, wherein a rare particle characteristic is detected in an aliquot during operation of a simultaneous mode. Briefly, a cell suspension containing undesirable cells (101) and desirable rare cells (102) is directed to flow from left to right in a flow channel (103). Multiple cells may traverse a detection volume (104) enclosed by a shaded cylinder at a given time and be detected simultaneously. If no desired cells are detected, an aliquot equivalent to the detection volume is ranked as null and directed toward Channel 111. If any desired cells are detected, the aliquot is ranked as nonzero and is directed toward Channel 121.

A filter element (122) may optionally be disposed in Channel 121 to selectively allow the passage of the fluid portion while retaining the desired bioparticles. The filter element may be in the form of microposts, microimpactors, microsieves, channels with apertures smaller than bioparticles, channels with apertures such that a bioparticle is prevented from entering an aperture but fluid is allowed to continue to flow around the bioparticle through the aperture ("1-D channels"), microbeads, porous membranes, protrusions from the walls, adhesive coating, woven or non-woven fibers (such as cloth or mesh) of wool, metal (e.g. stainless steel or Monel), glass, paper, or synthetic (e.g. nylon, polypropylene, polycarbonate, parylene, and polyester), sintered stainless steel or other metals, or porous inorganic materials such as alumina, silica, or carbon.

I. Example 9

Figure 2:
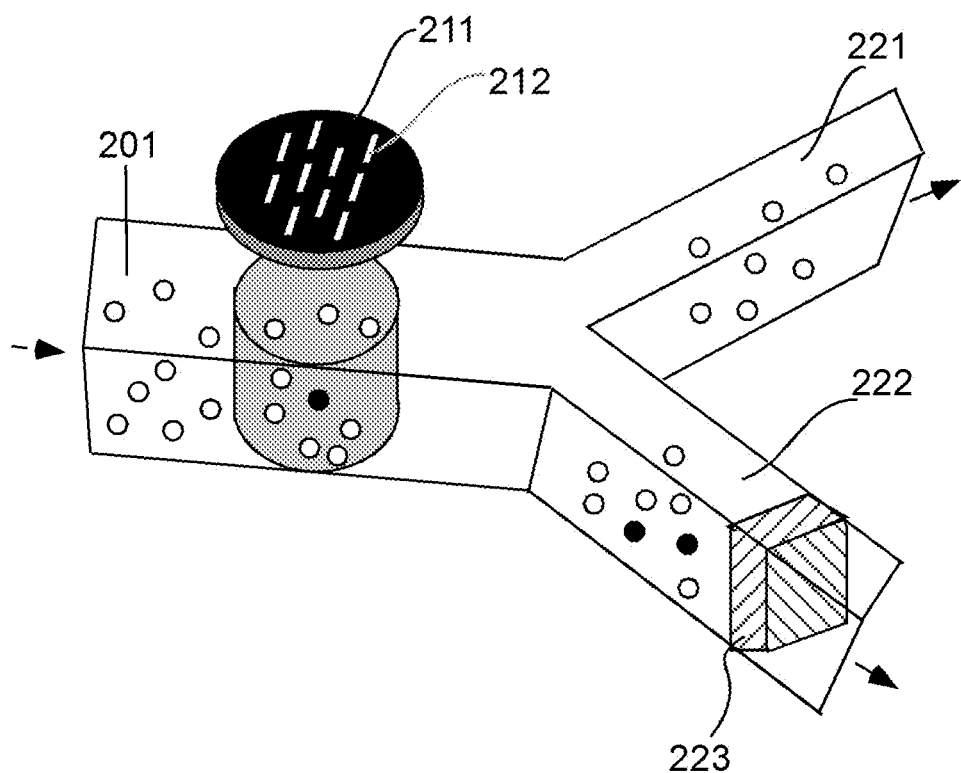
FIG. 2 illustrates a mask with apertures to improve the signal-to-noise ratio as used in eDAR.

In another example of eDAR run in a simultaneous mode, the method may further consist of selectively masking the aliquot as to reduce excessive background signal and improve the signal-to-noise ratio. FIG. 2 illustrates the use of a mask (211) with an array of apertures (212) positioned between the detection volume and a detector to selectively allow through a detectable characteristic. Multiple bioparticles still can be simultaneously detected with the use of the mask (211). By reducing excessive background signal and increasing the signal-to-noise ratio, the sensitivity of detection is enhanced as the weak signals from even a highly diluted aliquot can be accurately detected. In other words, the better the signal-to-noise ratio, larger an aliquot can be scanned. As a direct result, the fluidic throughput is correspondingly increased since fewer (but larger) aliquots need to be scanned. If no desired bioparticles are detected, an aliquot equivalent to the detection volume is ranked as null and directed toward Channel 221. If any desired bioparticles are detected, the aliquot is ranked as nonzero and is directed toward Channel 222.

J. Example 10

FIG. 11A, which is an enlarged illustration of device 710 (FIG. 7), illustrates device 1110, for aliquoting suspension with five fluidic channels (1111, 1112, 1113, 1114, and 1115) joined at junction 1116. Fluidic channels 1111, 1112, 1113 carried fluid toward junction 1116, whereas fluidic channels 1114 and 1115 carried fluid away from junction 1116. Solenoid piston 1120 was placed on top of channel 1111 and solenoid piston 1121 was placed on top of channel 1112. Solenoid pistons 1120 and 1121 were configured to push down on an elastomeric polydimethylsiloxane (PDMS) membrane, which separated the pistons 1120 and 1121 from the fluid in the channels 1111 and 1112.

FIG. 11A illustrates the operation of device 1110 for aliquoting suspension. By having solenoid piston 1120 pushing down on the PDMS membrane on top of flow channel 1111, channel 1111 was closed off. At the same time solenoid piston 1121 was configured to allow fluid to pass through channel 1112 toward junction 1116. As a result, blood containing rare cells in the incoming channel 1112 was diverted to left outlet channel 1114 (see FIG. 11B, 0 ms). To direct aliquot 1130 into the right outlet channel 1115, solenoid piston 1120 was retracted from the PDMS membrane on top of channel 1111 while solenoid piston 1121 pushed down the PDMS membrane on top of channel 1112. This resulted in directing an aliquot 1130 of blood containing rare cells into the right outlet channel 1115 (FIG. 11C, 5 ms and FIG. 11D, 10 ms). Aliquot redirecting using solenoid pistons as described required as little time as 5 ms.

K. Example 11

Figure 12A:
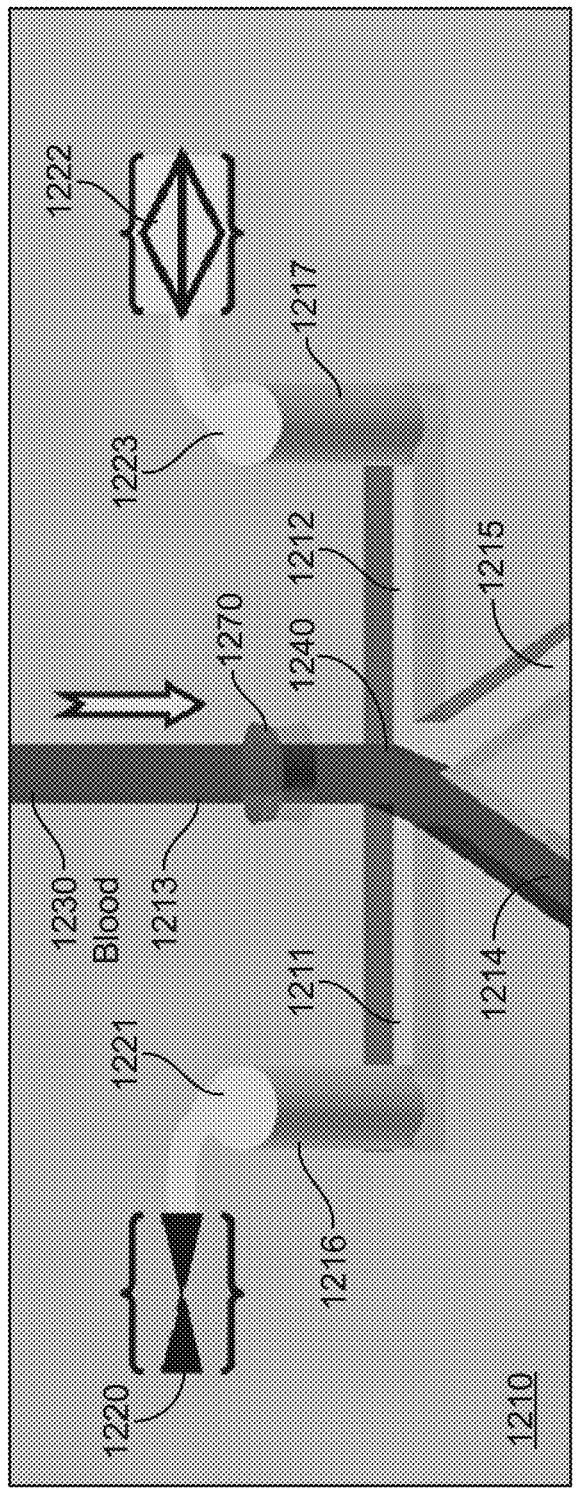
FIGS. 12A-12C illustrates device 1210 used for aliquoting suspension with five fluidic channels (1211, 1212, 1213, 1214, and 1215) joined at junction 1240.

FIG. 12A illustrates device 1210 used for aliquoting suspension with five fluidic channels (1211, 1212, 1213, 1214, and 1215) joined at junction 1240. Fluidic channels 1211, 1212, and 1213 carried fluid toward junction 1240, whereas fluidic channels 1214 and 1215 carried fluid away from junction 1240. Solenoid valve 1220 was connected to port 1216 in fluidic communication with channel 1211 via tubing 1221, and solenoid valve 1222 was connected to port 1217 in fluidic communication with channel 1212 via tubing 1223.

Figure 12B:
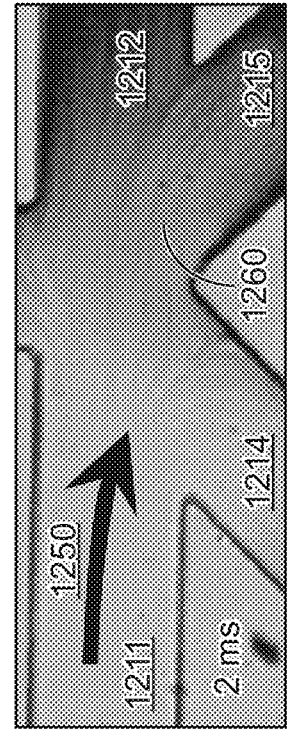
Figure 12C:
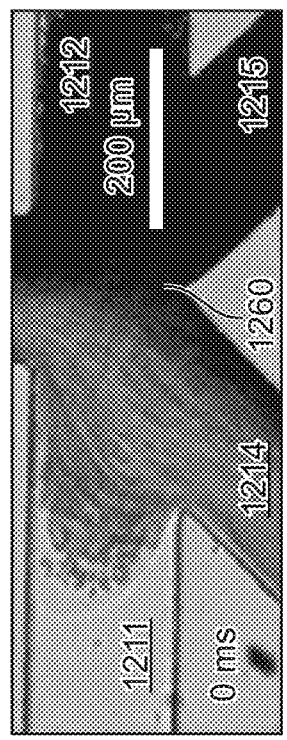

Solenoid valves 1220 and 1222 was actuated to close or open with electronic or computer signal (e.g. TTL signal). When solenoid valve 1220 was closed while solenoid valve 1222 remained open, aliquot 1260 of blood containing rare cells in the incoming channel 1213 was diverted to the left outlet channel 1214 (see FIG. 12B, 0 ms). When solenoid valve 1220 was opened while solenoid valve 1222 remained closed, aliquot 1260 of blood containing rare cells in the incoming channel 1213 was diverted to the right outlet channel 1215 (see FIG. 12C, 2 ms). Aliquot redirecting using a combination of solenoid valves 1220 and 1222 could channel the aliquot from one channel to another in as little as 2 ms.

L. Example 12

To test the performance of eDAR device, a mixture of blood and cancer cells was prepared according to the following procedure: 1×10E6/mL MCF-7 cells were labeled with 20 µL of fluorescent EpCAM antibody. This cell mixture was then diluted to 1×10E5 cells/mL with Isoton hematological diluent. Ten µL of the diluted cell mixture was then added to 2 mL of whole human blood and flowed through the aliquoting device. The flow rate in the aliquoting device was nominally 30 µL/min unless otherwise indicated.

Figure 13:
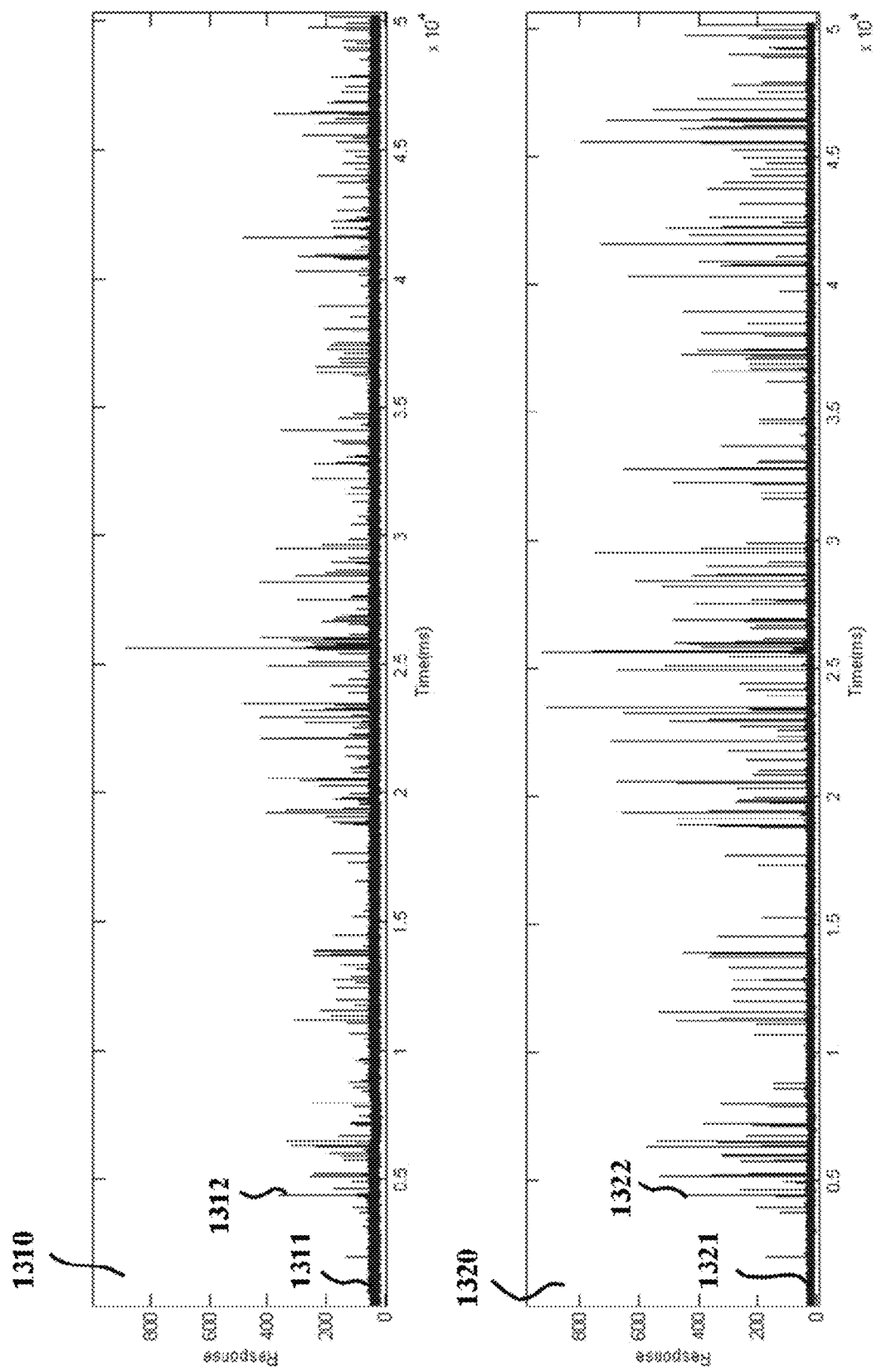
FIG. 13 shows the fluorescence signals collected from 2 avalanche photodiodes (APDs) positioned at different locations upstream and downstream of junction 1116 (or 1240). Plot 1310 shows the signal trace 1311 from one APD configured to detect the presence of EpCAM molecule in an aliquot at detection volume 1140 (or 1270), whereas Plot 1320 shows the signal trace 1321 from a second APD configured to detect the presence of EpCAM molecule in channel 1114 (or 1214).

FIG. 13 shows the fluorescence signals collected from 2 avalanche photodiodes (APDs) positioned at different locations upstream and downstream of junction 1116 (or 1240). Plot 1310 shows the signal trace 1311 from one APD configured to detect the presence of EpCAM molecule in an aliquot at detection volume 1140 (or 1270), whereas Plot 1320 shows the signal trace 1321 from a second APD configured to detect the presence of EpCAM molecule in channel 1114 (or 1214). The signal peaks 1312 matched substantially the signal peaks 1322, indicating that channeling of aliquot was correct, resulting in a high recovery of rare cells.

Figure 14:
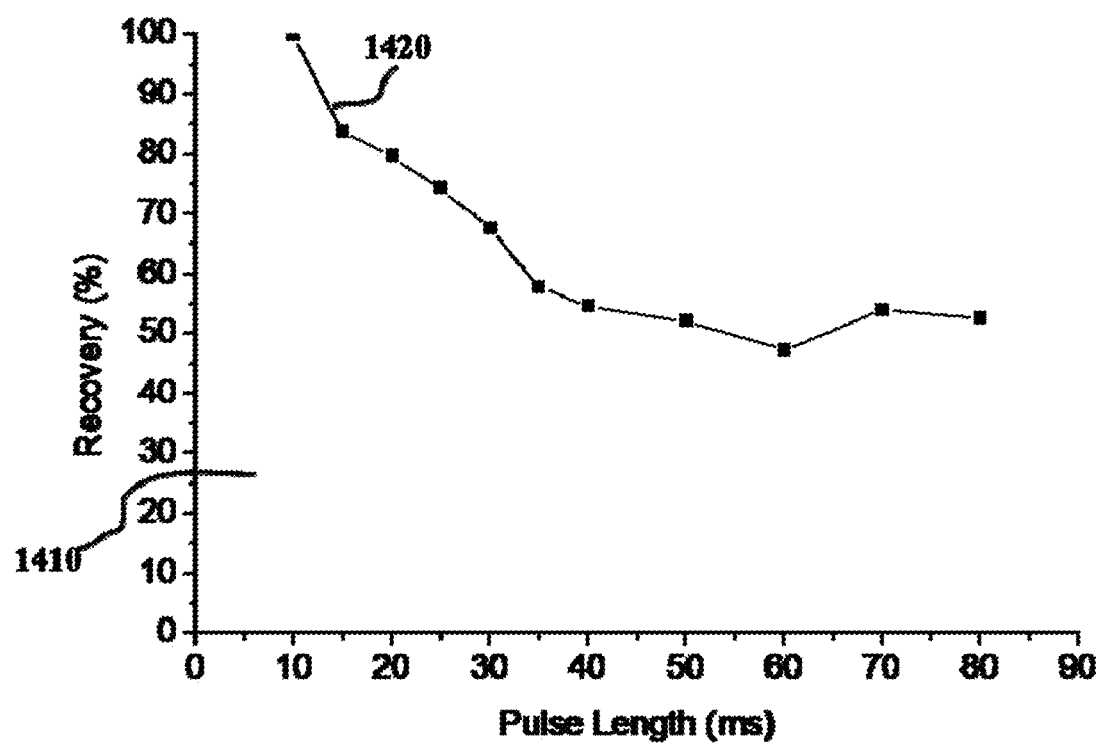
FIG. 14 shows plot 1410 illustrating the percentage of cancer cells recovered as a function of the pulse length using eDAR. Trace 1420 indicates that when the pulse width was 10 ms or below, 100% of the cancer cells were collected in the correct channel.

To further investigate the performance of eDAR device, the number of cancer cells directed into the correct flow channel were counted and subsequently collected ("recovered") while adjusting the length of time the solenoid valve (1220, 1222) or piston (1120, 1121) remain closed or open ("pulse length"). The percentage recovery was computed by dividing the number of rare cells collected in the correct channel by the number of rare cells detected by an APD at detection volume 1140 or 1270. FIG. 14 Plot 1410 shows the percentage of cancer cells recovered as a function of the pulse length. Trace 1420 indicates that when the pulse width was 10 ms or below, 100% of the cancer cells were collected in the correct channel. As pulse width increased, trace 1420 decreased, indicating a loss of cells to the wrong channel.

Figure 15:
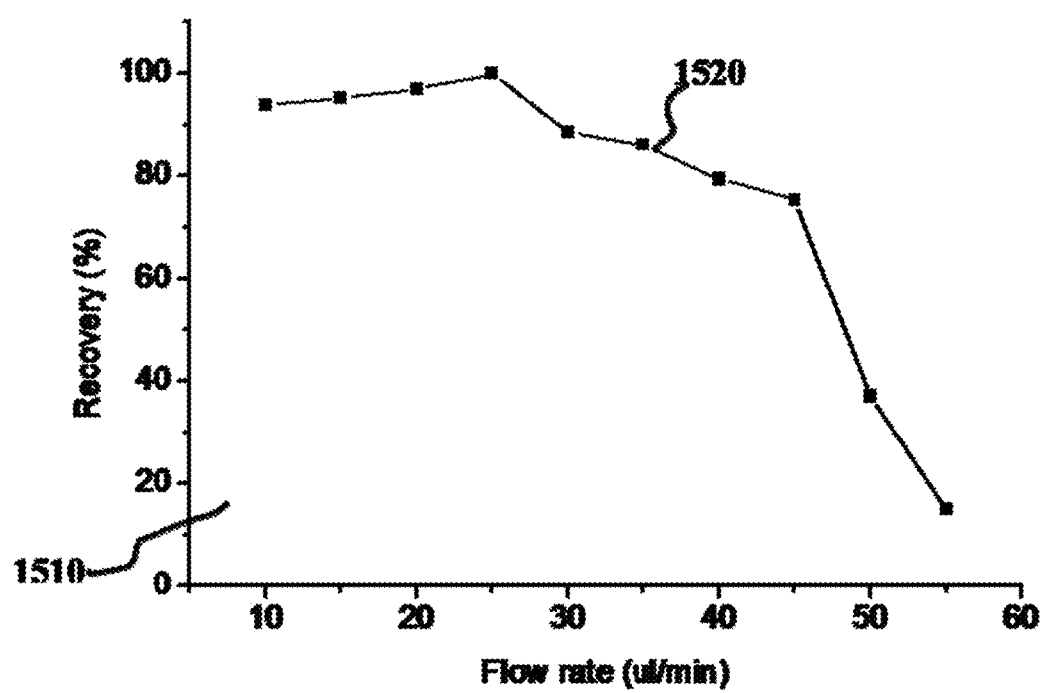
FIG. 15 shows plot 1510 with trace 1520 indicating the percentage of rare cells recovered as a function of incoming flow rate.

By adjusting the flow rate of incoming channel 1113 (or 1213), we also observed that the recovery could be optimized. FIG. 15 shows plot 1510 with trace 1520 indicating the percentage of rare cells recovered as a function of incoming flow rate. When the flow rate was below 30 µL/min, the recovery was between 89-100%. However, as the flow rate increased, the recovery decreased, indicating an increasing loss of rare cells in the wrong channel.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for detecting a rare cell in a fluid sample comprising other cell population, the method comprising the steps of:
    (a) partitioning the fluid sample into plurality of aliquots, wherein the rare cell is a fluorescently labelled cell configured to express a fluorescent protein or the rare cell is labeled with a fluorescent detection reagent and wherein the rare cell is a cell present in the fluid sample at a low level comprising less than about 1 part per $10^3$ of the total cell population in the fluid sample;
    (b) detecting, with a detector, the presence or absence of a rare cell in each of the plurality of aliquots of the fluid sample, wherein the aliquot comprises a plurality of cells randomly distributed in a three-dimensional detection volume of the detector during detection, wherein the step of detecting the presence or absence of the rare cell comprises the sub-steps of:

(i) illuminating simultaneously the plurality of cells of the aliquot with an external source of electromagnetic radiation; and (ii) detecting in the illuminated aliquot fluorescence from the plurality of cells including the rare cell; and (c) ranking each of the plurality of aliquots as a null or nonzero based on the absence or presence respectively of the fluorescence detected in each of the plurality of aliquots, and directing the flow of the aliquot to discard when the aliquot is ranked as null and directing the flow to collection when the aliquot is ranked as nonzero.

2. The method of claim 1, wherein the individual aliquots are not physically separated.

3. The method of claim 1, wherein the aliquot comprises a discrete volume containing the plurality of cells.

4. The method of claim 1, wherein the aliquot contains more than one rare cell.

5. The method of claim 1, wherein the detection step is performed during continuous flow of the aliquet through a flow channel.

6. The method of claim 1, wherein a plurality of aliquots of the fluid sample are physically separated prior to the detection step.

7. The method of claim 6, wherein the aliquots are partitioned into separate flow channels or chambers prior to the detection step.

8. The method of claim 1, further comprising performing flow cytometry after step (c).

9. A method for detecting a rare cell in a fluid sample containing other cell population, the method comprising:

(a) contacting the fluid sample with a fluorescent detection reagent under conditions suitable to transform the detection reagent into a complex comprising the detection reagent and a rare cell, wherein the rare cell is present in the fluid sample at a low level comprising less than 1 part per $10^3$ of the total cell population; and partitioning the contacted fluid sample into plurality of aliquots;

(b) detecting, with a detector, the presence or absence of a complex formed in step (a) in each of the plurality of aliquots of the fluid sample, wherein the aliquot comprises a plurality of cells randomly distributed in a three-dimensional detection volume of the detector during detection, wherein the step of detecting the presence or absence of the complex comprises the sub-steps of:

(i) illuminating simultaneously the plurality of cells of the aliquot with an external source of electromagnetic radiation; and (ii) detecting in the illuminated aliquot fluorescence from the plurality of cells including the rare cell;

(c) ranking each of the plurality of aliquots as a null or nonzero based on the absence or presence respectively of the fluorescence detected in each of the plurality of aliquots and directing the flow of the aliquots by channeling the aliquots based on the ranking of null or nonzero, wherein the aliquot is directed into a first channel or waste outlet when the ranking is null and the aliquot is directed to second channel or a first collection chamber when the ranking is nonzero.

* * * * *